United States Patent
Lee et al.

(10) Patent No.: US 10,357,215 B2
(45) Date of Patent: Jul. 23, 2019

(54) COMPUTED TOMOGRAPHIC APPARATUS AND METHOD FOR CONTROLLING THE SAME

(71) Applicant: SAMSUNG ELECTRONICS CO., LTD., Suwon-si (KR)

(72) Inventors: Duhgoon Lee, Suwon-si (KR); Gun Woo Lee, Seoul (KR); Mi Hee Bang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 255 days.

(21) Appl. No.: 14/870,220

(22) Filed: Sep. 30, 2015

(65) Prior Publication Data
US 2016/0157799 A1 Jun. 9, 2016

(30) Foreign Application Priority Data
Dec. 5, 2014 (KR) ........................ 10-2014-0174122

(51) Int. Cl.
*A61B 6/03* (2006.01)
*A61B 6/00* (2006.01)

(52) U.S. Cl.
CPC .............. *A61B 6/482* (2013.01); *A61B 6/032* (2013.01); *A61B 6/4208* (2013.01);
(Continued)

(58) Field of Classification Search
CPC ..... A61B 6/032; A61B 6/4208; A61B 6/4233; A61B 6/4241; A61B 6/46; A61B 6/463; A61B 6/48; A61B 6/482; A61B 6/488
(Continued)

(56) References Cited

U.S. PATENT DOCUMENTS

| | | | | |
|---|---|---|---|---|
| 5,155,365 A | * | 10/1992 | Cann .................... | A61B 6/4241 |
| | | | | 250/363.02 |
| 5,247,559 A | * | 9/1993 | Ohtsuchi .............. | A61B 6/4035 |
| | | | | 378/53 |

(Continued)

FOREIGN PATENT DOCUMENTS

| | | |
|---|---|---|
| JP | 2008142389 A | 6/2008 |
| KR | 1020140017339 A | 2/2014 |

(Continued)

OTHER PUBLICATIONS

Communication dated Jan. 9, 2017 issued by the Korean Intellectual Property Office in counterpart Korean patent Application No. 10-2014-0174122.

(Continued)

*Primary Examiner* — Allen C. Ho
(74) *Attorney, Agent, or Firm* — Sughrue Mion, PLLC

(57) ABSTRACT

A computed tomographic (CT) apparatus and for a method of controlling the same are provided. The CT apparatus includes an X-ray scanner configured to divide X-rays penetrating a subject by energy bands, and capture scout images of the respective energy bands. The CT apparatus further includes an image processor configured to generate substance images of substances of the subject, based on the scout images, and a display configured to display a substance image of the substance images. The CT apparatus further includes an input interface configured to receive a scanning region for the displayed substance image.

29 Claims, 26 Drawing Sheets

(52) U.S. Cl.
CPC .......... *A61B 6/4233* (2013.01); *A61B 6/4241* (2013.01); *A61B 6/46* (2013.01); *A61B 6/463* (2013.01); *A61B 6/48* (2013.01); *A61B 6/488* (2013.01)

(58) Field of Classification Search
USPC .............................. 378/19, 98.8; 250/370.09
See application file for complete search history.

(56) References Cited

U.S. PATENT DOCUMENTS

| | | | | |
|---|---|---|---|---|
| 6,341,152 B1* | 1/2002 | Sugihara | ................ | A61B 6/032 378/20 |
| 6,813,333 B2* | 11/2004 | Karau | ................... | A61B 6/032 378/4 |
| 6,898,263 B2* | 5/2005 | Avinash | ................ | A61B 6/032 378/4 |
| 6,950,492 B2* | 9/2005 | Besson | ................ | A61B 6/032 378/16 |
| 6,950,493 B2* | 9/2005 | Besson | ................ | A61B 6/032 378/16 |
| 6,990,171 B2* | 1/2006 | Toth | ....................... | A61B 6/032 378/158 |
| 6,999,549 B2* | 2/2006 | Sabol | ................... | A61B 5/4872 378/5 |
| 7,031,425 B2* | 4/2006 | Hsieh | ..................... | A61B 6/022 378/5 |
| 7,072,437 B2* | 7/2006 | Seto | ....................... | A61B 6/032 378/162 |
| 7,209,536 B2* | 4/2007 | Walter | ................... | A61B 6/032 378/5 |
| 7,289,596 B2* | 10/2007 | Horiuchi | ............. | G01N 23/046 378/4 |
| 7,532,703 B2* | 5/2009 | Du | ........................ | A61B 6/032 378/116 |
| 7,573,040 B2* | 8/2009 | Tkaczyk | ................ | G01T 1/249 250/370.09 |
| 7,613,274 B2* | 11/2009 | Tkaczyk | ................ | A61B 6/032 378/19 |
| 7,680,240 B2* | 3/2010 | Manjeshwar | .......... | A61B 6/032 378/4 |
| 7,684,537 B2* | 3/2010 | Imai | ...................... | A61B 6/405 378/16 |
| 7,696,483 B2* | 4/2010 | Tkaczyk | ................ | G01T 1/171 250/370.06 |
| 7,715,522 B2* | 5/2010 | Goto | ...................... | A61B 6/032 378/16 |
| 7,724,865 B2* | 5/2010 | Wu | ........................ | A61B 6/032 378/4 |
| 7,829,860 B2* | 11/2010 | Nygard | ................ | G01T 1/2018 250/366 |
| 7,852,978 B2* | 12/2010 | Proksa | ................ | G01T 1/2985 378/19 |
| 7,869,560 B2* | 1/2011 | Imai | ...................... | A61B 6/032 378/5 |
| 7,876,874 B2* | 1/2011 | Goto | ...................... | A61B 6/032 378/5 |
| 7,920,670 B2* | 4/2011 | Hugg | ..................... | A61B 6/032 378/4 |
| 7,920,674 B2* | 4/2011 | Kang | ..................... | A61B 6/4035 378/62 |
| 7,933,376 B2* | 4/2011 | Yoda | ........................ | A61B 6/04 378/205 |
| 7,983,383 B2* | 7/2011 | Kadomura | ............ | A61B 6/032 378/16 |
| 7,991,450 B2* | 8/2011 | Virtue | ................... | A61B 6/032 382/128 |
| 8,000,510 B2* | 8/2011 | Boeing | ................ | A61B 6/482 250/370.08 |
| 8,160,206 B2* | 4/2012 | Wu | ........................ | A61B 6/032 378/4 |
| 8,189,736 B2* | 5/2012 | Hirokawa | ............ | A61B 6/032 378/15 |
| 8,213,566 B2* | 7/2012 | Roessl | ................. | A61B 5/4869 378/5 |
| 8,299,440 B2* | 10/2012 | Wainer | ................ | G01T 1/1647 250/363.04 |
| 8,338,791 B2* | 12/2012 | Proksa | ................... | G01T 1/171 250/369 |
| 8,373,135 B2* | 2/2013 | Kappler | ............... | G01T 1/247 250/336.1 |
| 8,384,038 B2* | 2/2013 | Guo | ....................... | G01T 1/247 250/370.09 |
| 8,401,266 B2* | 3/2013 | Xu | ........................ | G06T 11/008 382/100 |
| 8,422,636 B2* | 4/2013 | Greenberg | ................ | G01T 1/29 378/207 |
| 8,488,854 B2* | 7/2013 | Arenson | ............... | G06T 11/005 378/1 |
| 8,513,614 B2* | 8/2013 | Kraft | ..................... | G01T 1/1647 250/370.09 |
| 8,538,116 B2* | 9/2013 | Jang | ...................... | G06T 11/005 382/131 |
| 8,548,118 B2* | 10/2013 | Hsieh | ..................... | A61B 6/482 378/124 |
| 8,649,478 B2* | 2/2014 | Kobayashi | ............. | A61B 6/032 378/4 |
| 8,649,480 B2* | 2/2014 | Yoshida | ................. | A61B 6/032 378/16 |
| 8,653,471 B2* | 2/2014 | Proksa | ................... | A61B 6/032 250/363.01 |
| 8,798,230 B2* | 8/2014 | Cho | ........................ | A61B 6/405 378/15 |
| 8,837,801 B2* | 9/2014 | Jang | ........................ | A61B 6/00 382/132 |
| 8,913,711 B2* | 12/2014 | Moriyasu | ................. | A61B 6/03 378/4 |
| 8,927,937 B2* | 1/2015 | Schwarzman | .......... | G01T 1/244 250/370.01 |
| 8,941,076 B2* | 1/2015 | Abraham | ................ | G01T 1/171 250/336.1 |
| 8,965,095 B2* | 2/2015 | Zou | ........................ | G06T 11/005 378/4 |
| 8,988,267 B1* | 3/2015 | Kimura | ................. | G01T 1/2928 341/155 |
| 9,014,455 B2* | 4/2015 | Oh | .......................... | A61B 6/52 378/98.11 |
| 9,052,266 B2* | 6/2015 | Miyazaki | ............. | A61B 6/4241 |
| 9,055,919 B2* | 6/2015 | Proksa | ................ | A61B 5/4869 |
| 9,084,542 B2* | 7/2015 | Bouhnik | ............. | A61B 6/032 |
| 9,111,379 B2* | 8/2015 | Gregerson | ............ | G06T 11/003 |
| 9,119,560 B2* | 9/2015 | Kohara | ................ | A61B 6/032 |
| 9,149,241 B2* | 10/2015 | Kim | ........................ | A61B 6/482 |
| 9,160,939 B2* | 10/2015 | Funaki | ................... | H03M 1/145 |
| 9,208,585 B2* | 12/2015 | Leng | ..................... | A61B 6/032 |
| 9,237,874 B2* | 1/2016 | DeMan | ................ | A61B 6/032 |
| 9,268,035 B2* | 2/2016 | Herrmann | ................ | G01T 1/17 |
| 9,269,168 B2* | 2/2016 | Inglese | ................ | A61B 6/4241 |
| 9,274,037 B2* | 3/2016 | Huwer | .................... | A61B 6/505 |
| 9,301,378 B2* | 3/2016 | Steadman Booker | .... | G01T 1/24 |
| 9,310,490 B2* | 4/2016 | Abraham | ................ | G01T 1/17 |
| 9,316,745 B2* | 4/2016 | Noshi | ......................... | G01T 1/17 |
| 9,348,036 B2* | 5/2016 | Yamakawa | ................ | G01T 1/24 |
| 9,354,331 B2* | 5/2016 | Sagoh | ..................... | A61B 6/032 |
| 9,414,797 B2* | 8/2016 | Flohr | ..................... | A61B 6/032 |
| 9,417,339 B2* | 8/2016 | Spahn | .................... | G01T 1/247 |
| 9,418,451 B2* | 8/2016 | Taguchi | ................ | G06T 11/003 |
| 9,423,515 B2* | 8/2016 | Roessl | .................... | G01T 1/241 |
| 9,456,790 B2* | 10/2016 | Taguchi | ................ | A61B 6/4241 |
| 9,504,438 B2* | 11/2016 | Proksa | .................... | G01T 1/24 |
| 9,517,045 B2* | 12/2016 | Kang | ..................... | G01N 23/087 |
| 9,532,759 B2* | 1/2017 | Taguchi | ................. | A61B 6/032 |
| 9,538,107 B2* | 1/2017 | Chappo | ................. | A61B 6/032 |
| 9,547,889 B2* | 1/2017 | Goshen | ................... | G06T 5/002 |
| 9,579,075 B2* | 2/2017 | Besson | ................ | G01T 1/2985 |
| 9,585,626 B2* | 3/2017 | Gao | ....................... | A61B 6/032 |
| 9,588,239 B2* | 3/2017 | Abraham | ................ | G01T 1/247 |
| 9,595,101 B2* | 3/2017 | Kato | ..................... | G06T 11/005 |
| 9,606,058 B2* | 3/2017 | Rothberg | ............ | G01N 21/6408 |
| 9,610,055 B2* | 4/2017 | Taguchi | ................. | A61B 6/5205 |

(56) References Cited

U.S. PATENT DOCUMENTS

| | | | |
|---|---|---|---|
| 9,642,588 B2 * | 5/2017 | Goto | A61B 6/542 |
| 9,645,260 B2 * | 5/2017 | Abraham | G01T 1/247 |
| 9,649,081 B2 * | 5/2017 | Kang | A61B 6/405 |
| 9,655,580 B2 * | 5/2017 | Jin | A61B 6/03 |
| 9,655,584 B2 * | 5/2017 | Lee | A61B 6/542 |
| 9,662,077 B2 * | 5/2017 | Moriyasu | A61B 6/4241 |
| 9,662,078 B2 * | 5/2017 | Berglund | A61B 6/4233 |
| 9,664,798 B2 * | 5/2017 | Kappler | G01T 1/17 |
| 9,678,220 B2 * | 6/2017 | Herrmann | G01T 1/17 |
| 9,693,743 B2 * | 7/2017 | Arakita | G01T 1/1606 |
| 9,706,973 B2 * | 7/2017 | Takamatsu | A61B 6/482 |
| 9,713,452 B2 * | 7/2017 | Narayanan | A61B 6/032 |
| 9,724,061 B2 * | 8/2017 | Hyung | A61B 6/469 |
| 9,747,704 B2 * | 8/2017 | Taguchi | G06T 11/005 |
| 9,759,822 B2 * | 9/2017 | Daerr | G01T 1/17 |
| 9,795,353 B2 * | 10/2017 | Teshigawara | A61B 6/032 |
| 9,808,210 B2 * | 11/2017 | Yamazaki | A61B 6/032 |
| 9,841,389 B2 * | 12/2017 | Tamura | G01N 23/046 |
| 9,870,628 B2 * | 1/2018 | Gronberg | G01N 23/046 |
| 9,872,661 B2 * | 1/2018 | Ono | A61B 6/5205 |
| 9,901,318 B2 * | 2/2018 | Kang | G01N 23/04 |
| 9,924,910 B2 * | 3/2018 | Klahr | A61B 6/032 |
| 9,924,916 B2 * | 3/2018 | Kato | A61B 6/4241 |
| 9,949,710 B2 * | 4/2018 | Kang | A61B 6/481 |
| 9,959,640 B2 * | 5/2018 | Koehler | G06T 11/60 |
| 9,971,047 B2 * | 5/2018 | Tamura | G01T 1/2985 |
| 9,986,957 B2 * | 6/2018 | Cho | G01N 23/02 |
| 10,012,600 B2 * | 7/2018 | Kang | G01N 23/04 |
| 10,024,807 B2 * | 7/2018 | Yamakawa | A61B 6/02 |
| 10,043,293 B2 * | 8/2018 | Ida | A61B 6/032 |
| 10,074,197 B2 * | 9/2018 | Nitta | G06T 11/005 |
| 10,080,533 B2 * | 9/2018 | Roessl | A61B 6/032 |
| 10,117,628 B2 * | 11/2018 | Tamura | A61B 6/032 |
| 10,139,354 B2 * | 11/2018 | Persson | A61B 6/482 |
| 10,154,821 B2 * | 12/2018 | Kawata | A61B 6/032 |
| 10,159,450 B2 * | 12/2018 | Kato | A61B 6/52 |
| 10,165,995 B2 * | 1/2019 | Eusemann | A61B 6/032 |
| 10,185,044 B2 * | 1/2019 | Noshi | A61B 6/032 |
| 10,206,638 B2 * | 2/2019 | Nakai | A61B 6/4241 |
| 10,217,246 B2 * | 2/2019 | Takayama | G01N 23/046 |
| 10,219,763 B2 * | 3/2019 | Kojima | A61B 6/4241 |
| 2004/0101086 A1 | 5/2004 | Sabol et al. | |
| 2004/0101087 A1 | 5/2004 | Hsieh et al. | |
| 2010/0040268 A1 | 2/2010 | Boeing et al. | |
| 2011/0150175 A1 | 6/2011 | Hsieh et al. | |
| 2014/0003572 A1 | 1/2014 | Gregerson et al. | |
| 2014/0086383 A1 | 3/2014 | Huwer et al. | |
| 2014/0187932 A1 | 7/2014 | Li et al. | |

FOREIGN PATENT DOCUMENTS

| | | |
|---|---|---|
| KR | 1020140057131 A | 5/2014 |
| WO | 2009/141766 A2 | 11/2009 |

OTHER PUBLICATIONS

Communication dated May 17, 2017, issued by European Patent Office in counterpart European Application No. 15187528.3.

Communication dated Apr. 22, 2016, issued by European Patent Office in counterpart European Application No. 15187528.3.

Communication dated Jan. 12, 2016, issued by the Korean Intellectual Property Office in counterpart Korean Application No. 10-2014-0174122.

Communication dated May 8, 2018, issued by European Patent Office in counterpart European Application No. 15187528.3.

Communication dated Apr. 9, 2019, issued by the European Patent Office in counterpart European Application No. 15187528.3.

* cited by examiner

142

142

142

142

142

142

142

142

142

142

142

142

142

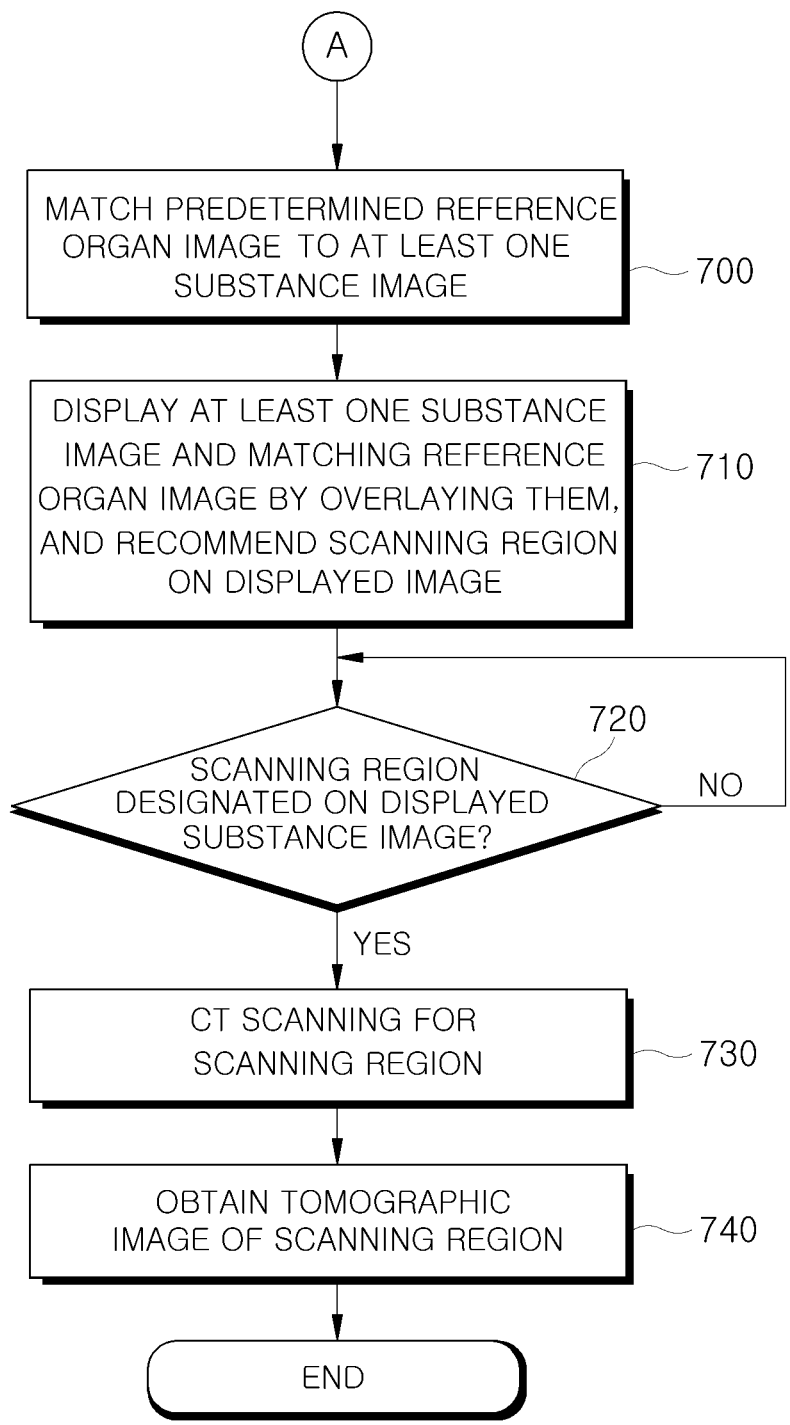

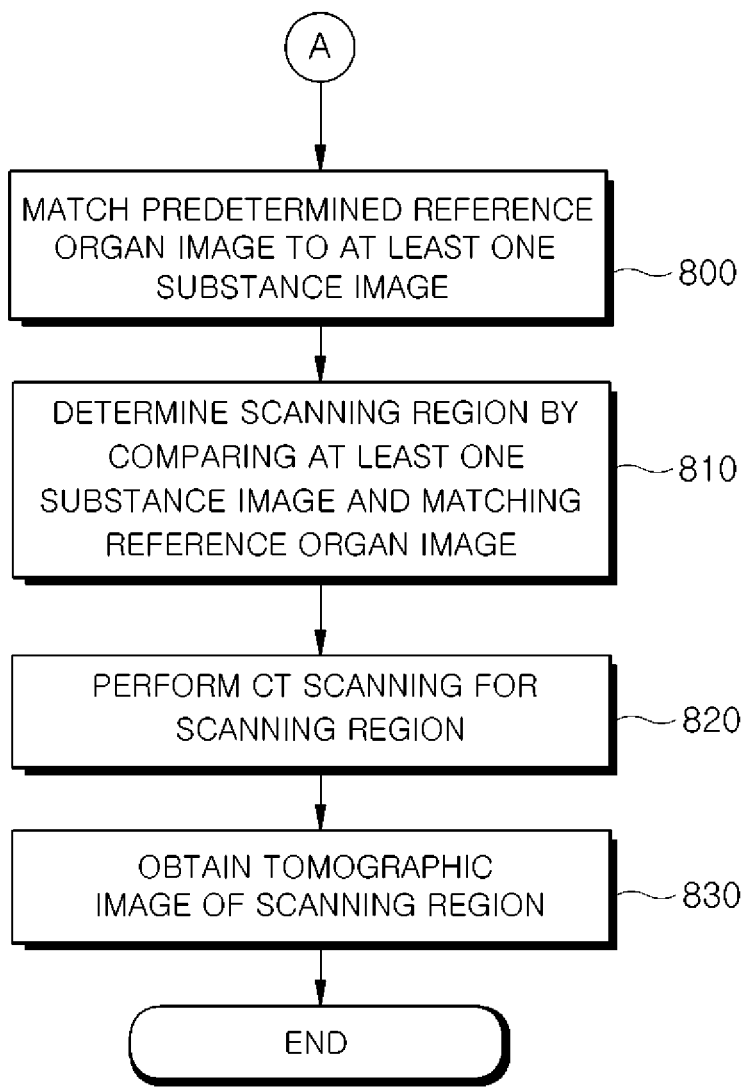

COMPUTED TOMOGRAPHIC APPARATUS AND METHOD FOR CONTROLLING THE SAME

CROSS-REFERENCE TO RELATED APPLICATION

This application claims priority from Korean Patent Application No. 10-2014-0174122, filed on Dec. 5, 2014, in the Korean Intellectual Property Office, the disclosure of which is incorporated herein by reference in its entirety.

BACKGROUND

1. Field

Apparatuses and methods consistent with exemplary embodiments relate to a computed tomographic apparatus and a method of controlling the same.

2. Description of the Related Art

X-ray imaging apparatuses are devices for allowing the user to see an internal structure of a subject by irradiating X-rays to the subject and using X-rays that passed through the subject. X-ray transmittance is different depending on the tissue of a subject, and the internal structure of the subject may be imaged using an attenuation coefficient quantified from the X-ray transmittance.

The X-ray imaging apparatus may be classified into a general radiographic apparatus for obtaining a projection image of the subject by transmitting X-rays from one direction, and a computed tomographic (CT) apparatus for reconstructing an image with a computer by transmitting X-rays in different directions. The CT apparatus is also referred to as a computed tomographic scanning apparatus, or computerized tomographic scanning apparatus.

For the CT apparatus to image a particular substance inside the subject, a region for scanning needs to be precisely established. Accordingly, a scout image for establishing the scanning region may be obtained before a CT scan is performed.

SUMMARY

Exemplary embodiments address at least the above problems and/or disadvantages and other disadvantages not described above. Also, the exemplary embodiments are not required to overcome the disadvantages described above, and may not overcome any of the problems described above.

Aspects of the exemplary embodiments provide a computed tomographic apparatus and a method of controlling the same, which provides a user with an image of a substance of a subject to receive an input of a scanning region from the user.

In accordance with an aspect of an exemplary embodiment, there is provided a computed tomographic (CT) apparatus including an X-ray scanner configured to divide X-rays penetrating a subject by energy bands, and capture scout images of the respective energy bands. The CT apparatus further includes an image processor configured to generate substance images of substances of the subject, based on the scout images, and a display configured to display a substance image of the substance images. The CT apparatus further includes an input interface configured to receive a scanning region for the displayed substance image.

The X-ray scanner may include an X-ray source configured to irradiate X-rays to the subject, and an X-ray detector configured to detect the X-rays penetrating the subject, and divide the detected X-rays by the energy bands. The X-ray scanner further includes a gantry on which the X-ray source and the X-ray detector are arranged to face each other.

The X-ray scanner may be further configured to capture the scout images by irradiating the X-rays to the subject moving in a direction parallel to a rotating shaft of the gantry, and perform CT scanning by rotating the gantry and irradiating X-rays to the received scanning region.

The image processor may be configured to separate the substance images from the scout images.

The display may be configured to display the substance image and a scout image of the scout images, the displayed substance image and the displayed scout image overlaying each other.

The controller may be further configured to match the substance image to a reference organ image, and the display may be configured to display a result of the matching.

The display may be configured to display the result of the matching and a scout image of the scout images, the displayed result of the matching and the displayed scout image overlaying each other.

The display may be configured to emphasize an organ region in the reference organ image.

The reference organ image may be determined based on information of an organ of the subject that is obtained from a sample.

The input interface may be further configured to receive an organ of interest among internal organs of the subject.

The display may be further configured to display the organ of interest as a recommended scanning region.

In accordance with an aspect of another exemplary embodiment, there is provided a computed tomographic (CT) apparatus including an X-ray scanner configured to divide X-rays penetrating a subject by energy bands, and capture scout images of the respective energy bands. The CT apparatus further includes an image processor configured to generate substance images of substances of the subject, based on the scout images, and a controller configured to determine a scanning region of the subject, based on a substance image of the substance images.

The X-ray scanner may be further configured to capture the scout images by irradiating the X-rays to the subject moving in a direction parallel to a rotating shaft of the gantry, and perform CT scanning by rotating the gantry and irradiating X-rays to the determined scanning region.

The controller may be configured to determine the scanning region by comparing the substance image and a reference organ image.

The controller may be further configured to match the substance image to a reference organ image, and determine the scanning region by comparing the matched substance image and the matched reference organ image.

The CT apparatus may further include an input interface configured to receive an organ of interest among internal organs of the subject.

The controller may be configured to determine the scanning region based on the organ of interest.

In accordance with an aspect of another exemplary embodiment, there is provided a method of controlling a computed tomographic (CT) apparatus, the method including dividing X-rays penetrating a subject by energy bands, capturing scout images of the respective energy bands. The method further includes generating substance images of substances of the subject, based on the scout images, displaying a substance image of the substance images, and receiving a scanning region for the displayed substance image.

The method may further include irradiating X-rays to the subject moving in a direction parallel to a rotating shaft of a gantry, and detecting the X-rays penetrating the subject. The dividing may include dividing the detected X-rays by the energy bands.

The method may further include performing CT scanning by rotating a gantry and irradiating X-rays to the received scanning region.

The displaying may include displaying the substance image and a scout image of the scout images, the displayed substance image and the displaying scout image overlaying each other.

The method may further include matching the substance image to a reference organ image, and the displaying may include displaying a result of the matching.

The method may further include receiving an organ of interest among internal organs of the subject, and displaying the organ of interest as a recommended scanning region.

In accordance with an aspect of another exemplary embodiment, there is provided a method of controlling a computed tomographic (CT) apparatus, the method including dividing X-rays penetrating a subject by energy bands, and capturing scout images of the respective energy bands. The method further includes generating substance images of substances of the subject, based on the scout images, and determining a scanning region of the subject, based on a substance image of the substance images.

The method may further include performing CT scanning by rotating a gantry and irradiating X-rays to the determined scanning region.

The method may further include matching the substance image to a reference organ image, and the determining may include determining the scanning region by comparing the matched substance image and the matched reference organ image.

The method may further include receiving an organ of interest among internal organs of the subject, and the determining may include determining the scanning region based on the organ of interest.

BRIEF DESCRIPTION OF THE DRAWINGS

The above and other aspects will become apparent and more readily appreciated from the following description of the exemplary embodiments, taken in conjunction with the accompanying drawings of which:

FIG. 17 is a flowchart illustrating a method of displaying multiple substance images included in a method of controlling a CT apparatus, according to another exemplary embodiment of the present disclosure; and FIG. 18 is a flowchart illustrating a method of controlling a CT apparatus, according to an exemplary embodiment of the present disclosure.

DETAILED DESCRIPTION OF THE EXEMPLARY EMBODIMENTS

Figure 1:
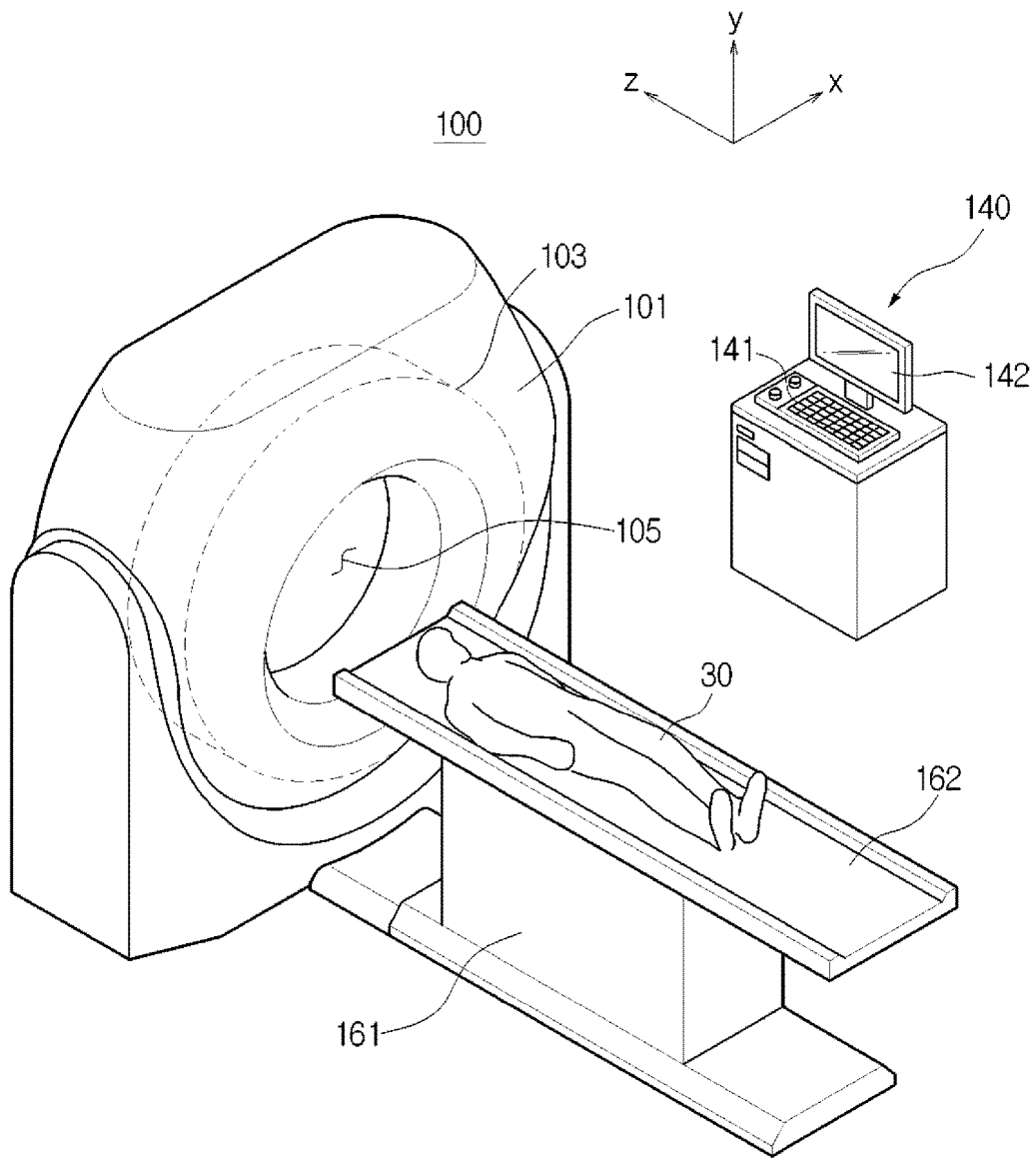
FIG. 1 is a perspective view illustrating a computed tomographic (CT) apparatus, according to an exemplary embodiment of the present disclosure.

A computed tomographic (CT) apparatus and method of controlling the same will now be described in detail with reference to accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those defined matters. Also, well-known functions or constructions are not described in detail because they would obscure the description with unnecessary detail.

The term 'subject' as herein used may refer to a patient, but is not limited thereto. In addition, the term 'user' as herein used may refer to a doctor, but is not limited thereto. In addition, the terms such as 'unit,' '-er (-or),' and 'module' described in the specification refer to an element configured to perform at least one function or operation, and may be implemented in hardware, software, or a combination of hardware and software.

Figure 2:
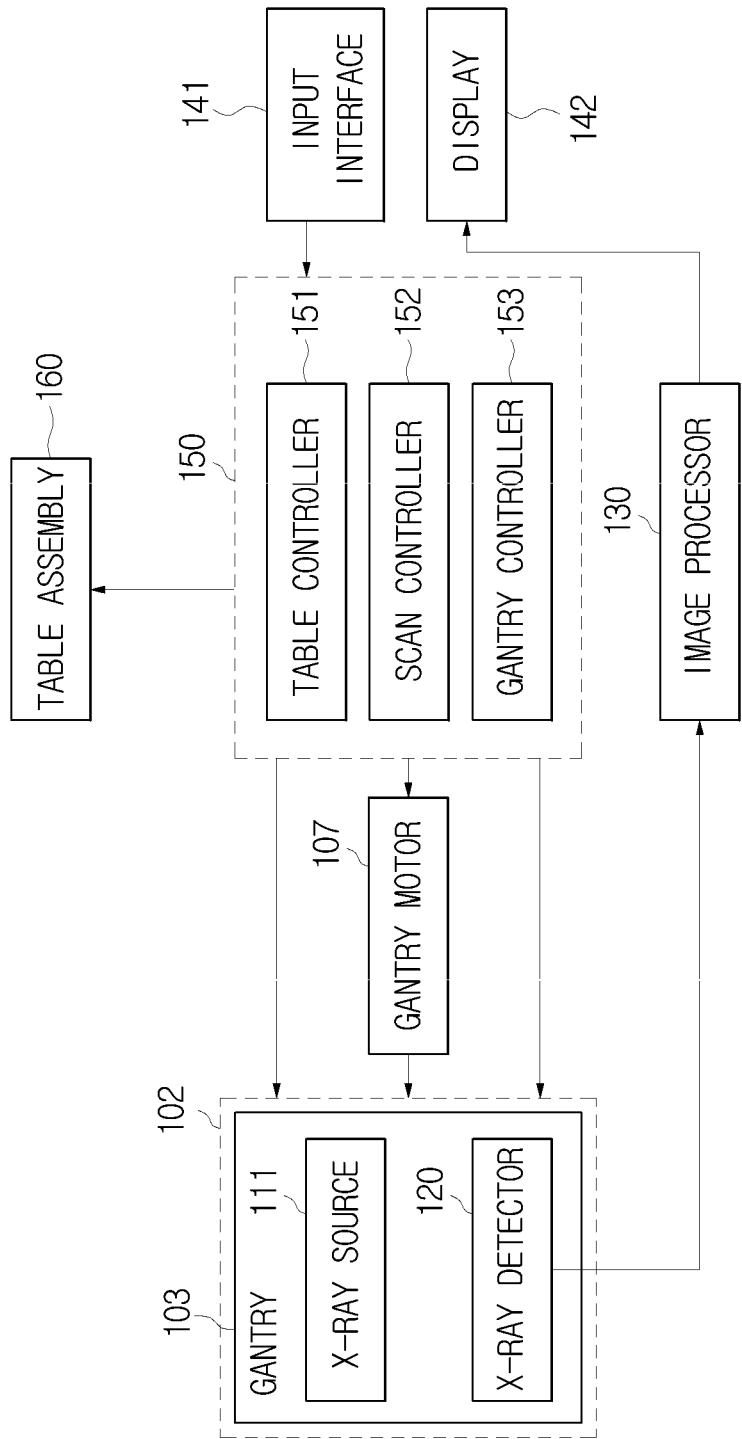
FIG. 2 is a control block diagram illustrating a CT apparatus, according to an exemplary embodiment of the present disclosure.

FIG. 1 is a perspective view illustrating a computed tomographic (CT) apparatus, according to an exemplary embodiment of the present disclosure. FIG. 2 is a control block diagram illustrating a CT apparatus, according to an exemplary embodiment of the present disclosure.

Referring to FIGS. 1 and 2, inside a housing 101 of a CT apparatus 100, an X-ray scanner 102 is arranged.

Figure 3:
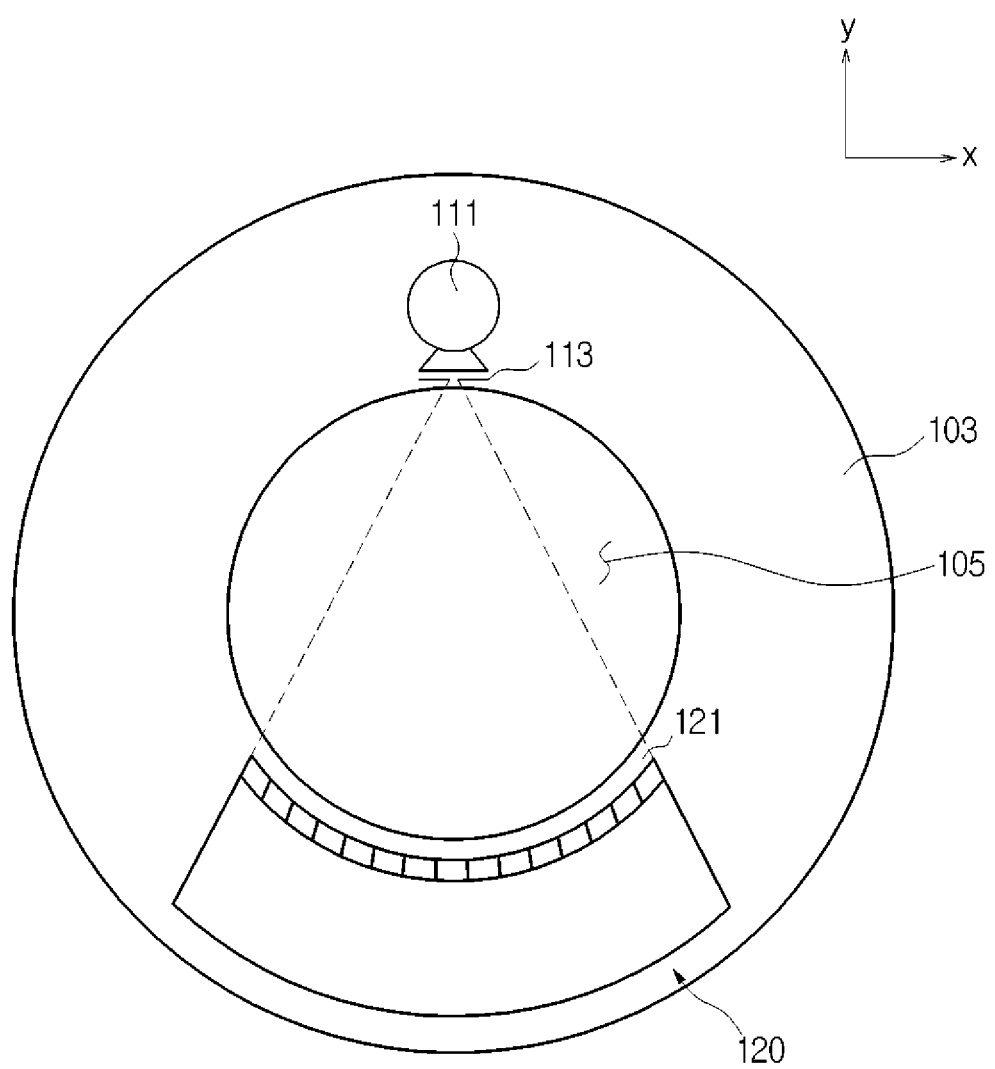
FIG. 3 is a cross-sectional view illustrating an X-ray scanner of a CT apparatus, according to an exemplary embodiment of the present disclosure.

The X-ray scanner 102 includes a gantry 103, inside which an X-ray source 111 and an X-ray detector 120 are mounted to face each other as shown in FIG. 3, the X-ray detector 120 detecting X-rays irradiated from the X-ray source 111.

A subject 30 is placed on a table assembly 160 having a patient table 162, on which the subject 30 lies, and a table supporter 161 for supporting the patient table 162. Inside the table supporter 161, there may be a driving device, such as a motor, a gear, etc., for supplying power to the patient table 162.

The patient table 162 is moved toward a bore 105 along the z-axis, and the subject 30 is then put within the bore 105. When the gantry 103 is rotated while the subject 30 is put within the bore 105, the X-ray source 111 irradiates X-rays while turning 360 degrees (turning a full circle) or more, and the X-rays penetrating the subject 30 may be detected by the X-ray detector 120.

The CT apparatus 100 includes a user interface for presenting the user with information and receiving control commands from the user, and the user interface includes an input interface 141 and a display 142. An apparatus equipped with the input interface 141 and the display 142 may be referred to as a workstation 140 or a host device.

Referring to FIG. 2, the CT apparatus 100 in accordance with an exemplary embodiment includes the X-ray scanner 102 including the X-ray source 111 for producing and irradiating X-rays to the subject 30 and the X-ray detector 120 for detecting X-rays that penetrate the subject 30, to obtain digital X-ray data. The CT apparatus 100 further includes a gantry motor 107 and a controller 150 for controlling the rotation of the gantry 103 and operations of the X-ray source 111 and the X-ray detector 120 equipped in the gantry 103. The CT apparatus 100 further includes the table assembly 160, and an image processor 130 for creating a tomographic image of the subject 30 by reconstructing the X-ray data. The CT apparatus 100 further includes the input interface 141 for receiving the user's command to control the CT apparatus 100, and the display 142 for displaying a screen related to controlling the CT apparatus 100 or a tomographic image of the subject 30.

The X-ray source 111 produces and irradiates X-rays having an energy band, and the X-ray detector 120 detects the X-rays, converts them to digital X-ray data, and sends the conversion result to the image processor 130. Details of the X-ray source 111 and X-ray detector 120 will be described below.

The image processor 130 reconstructs a tomographic image of the inside of the subject 30, using the X-ray data sent from the X-ray detector 120. As an image reconstruction method, there may be an iterative method, a direct Fourier method, a filtered back projection method, and the like.

Furthermore, the image processor 130 may compensate the data obtained from a counting detection region, using data obtained from an integrative detection region, as will be described later in detail.

The tomographic image reconstructed by the image processor 130 may be sent to the display 142, which in turn displays the tomographic image of the subject 30.

The input interface 141 and the display 142 may be included in the workstation 140. The input interface 141 may be implemented with at least one of various input devices, such as a mouse, a keyboard, a trackball, a touch panel, etc., and the display 142 may be implemented with at least one of various display devices, such as Light Emitting Diodes (LEDs), organic LEDs (OLEDs), Plasma Display Panel (PDP), Cathode-Ray Tube (CRT), etc.

The user may input control commands for all operation of the CT apparatus 100, including a command regarding movement of the patient table 162, a command regarding selection of scan mode, a command regarding scan condition, a command regarding image display, etc.

The display 142 may display a screen for helping the user input a control command, a screen for representing control status of the CT apparatus 100, and an image created by the image processor 130.

The controller 150 controls operations of the CT apparatus 100. The controller 150 includes a table controller 151 for controlling the movement of the patient table 162, a scan controller 152 for controlling scan-related parameters, scan mode, etc., by taking into account a scanning part of the subject 30, a purpose for diagnosis, characteristics of the subject 30, etc., and a gantry controller 153 for controlling rotation of the gantry 103, activation of the X-ray detector 120, etc.

The table controller 151 may control moving distance and moving direction of the patient table 162 for a target scanning region of the subject 30 that lies on the patient table 162 to be within the bore 105. For this, the table controller 151 may send a control signal to drive the patient table 162 to the table assembly 160.

The scan controller 152 may perform an Auto Exposure Controller (AEC) function that automatically controls exposure parameters, control a scan mode, and control activation of the X-ray detector 120 based on whether data is to be obtained from the integrative detection region or the counting detection region.

The scan controller 152 may control the exposure parameters, such as tube voltage, tube current, exposure time, filter type and thickness, target material of a positive electrode, focal spot size, etc., that are applied to the X-ray source 111, in performing the AEC function.

On the other hand, in case of controlling a scan mode, the scan controller 152 may control thickness or the number of slices obtained through one-time scanning, and determine which one of the counting detection region and integrative detection region is used to obtain respective slices in case of obtaining multiple slices or control activation of respective detection regions according to the determination result.

Moreover, it is also possible to selectively activate the counting detection region and the integrative detection region according to whether a multi-energy X-ray imaging scheme is applied.

The scan controller 152 may actively execute control or at the request of the user.

The gantry controller 153 may control the number of rotations or speed of rotation of the gantry 103, by sending a control signal to the gantry motor 107 that supplies a driving force for rotation to the gantry 103.

Figure 4:
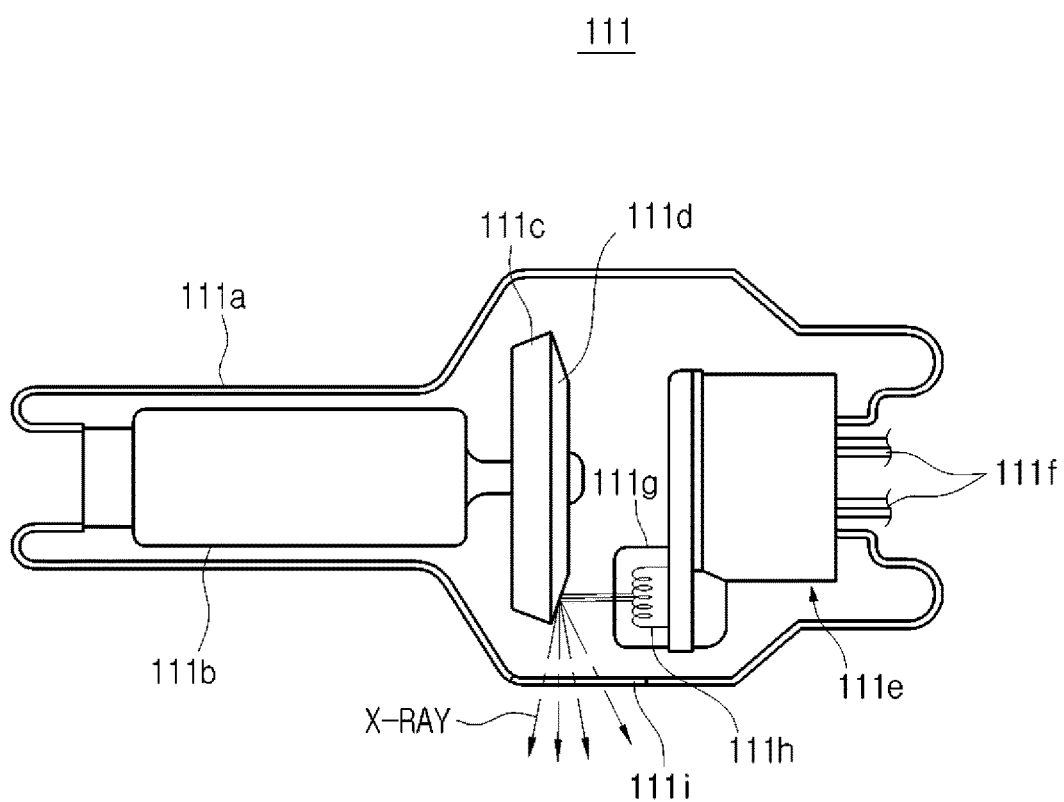
FIG. 4 is a cross-sectional view illustrating internal components of an X-ray source of a CT apparatus, according to an exemplary embodiment of the present disclosure.

FIG. 3 is a cross-sectional view illustrating the X-ray scanner 102 of the CT apparatus 100, according to an exemplary embodiment of the present disclosure. FIG. 4 is a cross-sectional view illustrating internal components of the X-ray source 111 of the CT apparatus 100, according to an exemplary embodiment of the present disclosure.

Referring to FIG. 3, the X-ray scanner 102 includes the gantry 103, and the X-ray source 111 and the X-ray detector 120 that are mounted inside the gantry 103 to face each other. The gantry 103 may rotate 360 degrees around the bore 105.

A collimator 113 is placed ahead of the X-ray source 111 in the direction of X-ray irradiation for controlling the width of an X-ray beam irradiated from the X-ray source 111. Accordingly, the collimator 113 may reduce beam scattering in other directions, thereby lowering the risk of the subject 30 being exposed to radiation.

It is also possible to arrange such the collimator 113 ahead of the X-ray detector 120 for detecting X-rays just within a region of interest. The collimator 113 arranged ahead of the X-ray detector 120 may cancel scattered rays, and control the width of an X-ray beam that penetrates the subject 30, thereby determining a thickness of the slice.

The X-ray source 111, also referred to as an X-ray tube, may be supplied with power from a power supply for producing X-rays.

Referring to FIG. 4, the X-ray source 111 is implemented with a two-pole vacuum tube including a positive electrode 111c and a negative electrode 111e. The negative electrode 111e includes a filament 111h and a focusing electrode 111g that focuses electrons, and the focusing electrode 111g is also called a focusing cup.

Thermions are generated by making the inside of a glass tube 111a in a high vacuum state of about 10 mmHg and heating the filament 111h of the negative electrode 111e to a high temperature. As an example of the filament 111h, a tungsten filament may be used, which may be heated by applying a current to an electric wire 111f coupled with the filament 111h.

The positive electrode 111c is mainly formed of copper, and a target material 111d is applied or disposed on the side that faces the negative electrode 111e, the target material 111d including a high resistive material, such as Cr, Fe, Co, Ni, W, Mo, or the like. The target material 111d is tilted at an angle, and the greater the tilting angle, the smaller the focus spot size. In addition, the focus spot size may vary depending on the tube voltage, tube current, size of the filament, size of the focusing electrode, distance between the positive electrode 111c and the negative electrode 111e.

When a high voltage is applied across the positive electrode 111c and the negative electrode 111e, thermions get accelerated and collide with the target material 111d of the positive electrode 111c, thus producing X-rays. The X-ray is irradiated out through a window 111i that may use a thin film of Beryllium. A filter may be placed on the front or rear side of the window 111i, to filter X-rays in an energy band.

The target material 111d may be rotated by a rotor 111b. While the target material 111d is rotating, heat build-up rate may increase more than ten times per unit area as compared with an occasion where the target material 111d is stationary, and the focal spot size may decrease.

A voltage applied across the positive electrode 111c and the negative electrode 111e of the X-ray source 111 is called a tube voltage whose magnitude may be represented by a crest value kVp. As the tube voltage increases, the speed of the thermion increases and as a result, energy of X-radiation (energy of photon radiation) from collision of the thermion with the target material 111d increases.

A current flowing in the X-ray source 111 is called a tube current, which may be represented by an average value mA. As the tube current increases, the number of thermions emitted from the filament increases and as a result, a dose of X-rays (the number of photons of X-rays) produced from collision with the target material 111d increases.

Accordingly, the energy of X-radiation may be controlled by the tube voltage, and the intensity or dose of X-rays may be controlled by the tube current and time for being exposed to X-rays. The energy, intensity or dose of X-rays may be determined depending on characteristics of the subject 30, such as type and thickness of the subject 30, or a purpose of diagnosis.

The X-ray source 111 may irradiate monochromatic X-rays or polychromatic X-rays. In the case the X-ray source 111 irradiates polychromatic X-rays in an energy band, the energy band of the X-rays to be irradiated may be defined by upper and lower limits.

The upper limit of the energy band, i.e., a maximum energy of X-rays to be irradiated, may be controlled by the level of the tube voltage, and the lower limit of the energy band, i.e., a minimum energy of X-rays to be irradiated, may be controlled by a filter arranged in the irradiation direction of the X-rays.

The filter may pass or filter out X-rays of an energy band. Accordingly, with the filter arranged on the front or back side of the window 111i for filtering the X-rays in an energy band, the X-rays of the energy band may be filtered.

For example, with a filter, such as aluminum or copper to filter X-rays of a low energy band which degrade the image quality, the X-ray beam quality may be hardened, thereby increasing the lower limit of the energy band and an average energy level of X-rays to be irradiated. It may further reduce radiation to which the subject 30 is exposed.

A bow-tie filter as will be described later in connection with FIG. 17 may serve as the filter, or a separate filter having the function as described above may exist in addition to the bow-tie filter.

Turning back to FIG. 3, a cross-section of the X-ray detector 120 may have the form of an arch, on the top of which detection elements 121 are arranged for detecting X-rays and converting them to electric signals.

The detection elements 121 may form an array of multiple detection elements, each detection element serving as a pixel.

The detection elements 121 may be classified by schemes for converting detected X-rays to electric signals or methods for obtaining electric signals, i.e., classified into those using a direct scheme and an indirect scheme for converting the detected X-rays to electric signals.

The detection elements 121 may also be divided into those having a charge integration mode for storing charges for a period of time and obtaining a signal from the charges and a photon counting mode for counting the number whenever a signal is generated by a single X-ray photon, based on the method of obtaining the electric signal.

In the direct conversion scheme, when X-ray is irradiated, a pair of electron and hole is generated temporarily inside the photo detector of the detection element 121, and electric potential across both terminals of the photo detector causes the electron to be moved to the positive electrode 111c and the hole to be moved to the negative electrode 111e. Accordingly, the detection element 121 converts the movements into an electric signal. In the direct conversion scheme, the material used for the photo detector may be e.g., a-Se, CdZnTe, HgI2, PbI2, etc.

In the indirect conversion scheme, a scintillator may be mounted on the top of the detection element 121, which is responsive to X-rays irradiated from the X-ray source 111 to emit photons having wavelengths of visible rays, and the photo detector may detect the photons and convert them to an electric signal. The material used for the photo detector in the indirect conversion scheme may be e.g., a-Si, and the scintillator may be a GADOX scintillator in the form of a thin film, or a micro column type or needle structure type CSI (T1).

The detection elements 121 may employ a proper one of the direct and indirect conversion schemes, and it is also possible that respective regions of the detection elements 121 as will be described later may use different conversion schemes. For example, the indirect conversion scheme may be applied for the integrative detection region, and the direct conversion scheme may be applied for the counting detection region.

In the meantime, in a case the photon counting scheme is used among the methods for obtaining electric signals, the inside of the subject 30 may be imaged even with a lower dose of radiation, and the image may have a good signal to noise (SNR) ratio.

In an exemplary embodiment of the CT apparatus 100, the detection elements 121 may use the photon counting scheme. Arrangement and structure of the detection elements 121 will now be described in detail.

The CT apparatus 100 may establish a scanning region before CT scanning of the subject 30. If information about a scanning region is input or designated by the user, the CT apparatus 100 may obtain a tomographic image of the scanning region.

For the user to designate a scanning region, the CT apparatus 100 may capture a scout image. The scout image may be an X-ray image of a part or entire region of the subject 30. The user may designate a scanning region, which is a target region for CT scanning, among the part or entire region of the subject 30.

If the scout image is obtained by a single energy of X-rays, the scout image may have unclear boundaries between substances that make up the subject 30. The user may then have difficulty designating a precise scanning region.

Accordingly, the CT apparatus 100 helps the user to designate a precise scanning region, by separating images of the substances (hereinafter, referred to as substance images) from the scout image.

The CT apparatus 100 that determines a scanning region based on the substance images will now be described in detail.

Turning back to FIG. 2, the CT apparatus 100 in accordance with an exemplary embodiment includes the X-ray scanner 102 for capturing a scout image to establish a scanning region of the subject 30, the image processor 130 for creating respective images of a plurality of substances that make up the subject 30 based on the captured scout image, the display 142 for displaying at least one of the multiple substance images, and the input interface 141 for receiving an input of a scanning region with respect to the displayed substance image.

As described above, the X-ray scanner 102 includes the X-ray source 111, the X-ray detector 120, and the gantry 103 having the X-ray source 111 and the X-ray detector 120 mounted thereon. The X-ray scanner 102 rotates the gantry 103, and performs CT scanning by irradiating X-rays to the scanning region of the subject 30 from the X-ray source 111 mounted on the rotating gantry 103. The gantry 103 may be rotated around a predetermined rotating shaft.

The X-ray scanner 102 also captures a scout image for establishing a scanning region, a target for CT scanning. A method of capturing a scout image using the X-ray scanner 102 will now be described.

Figure 5A:
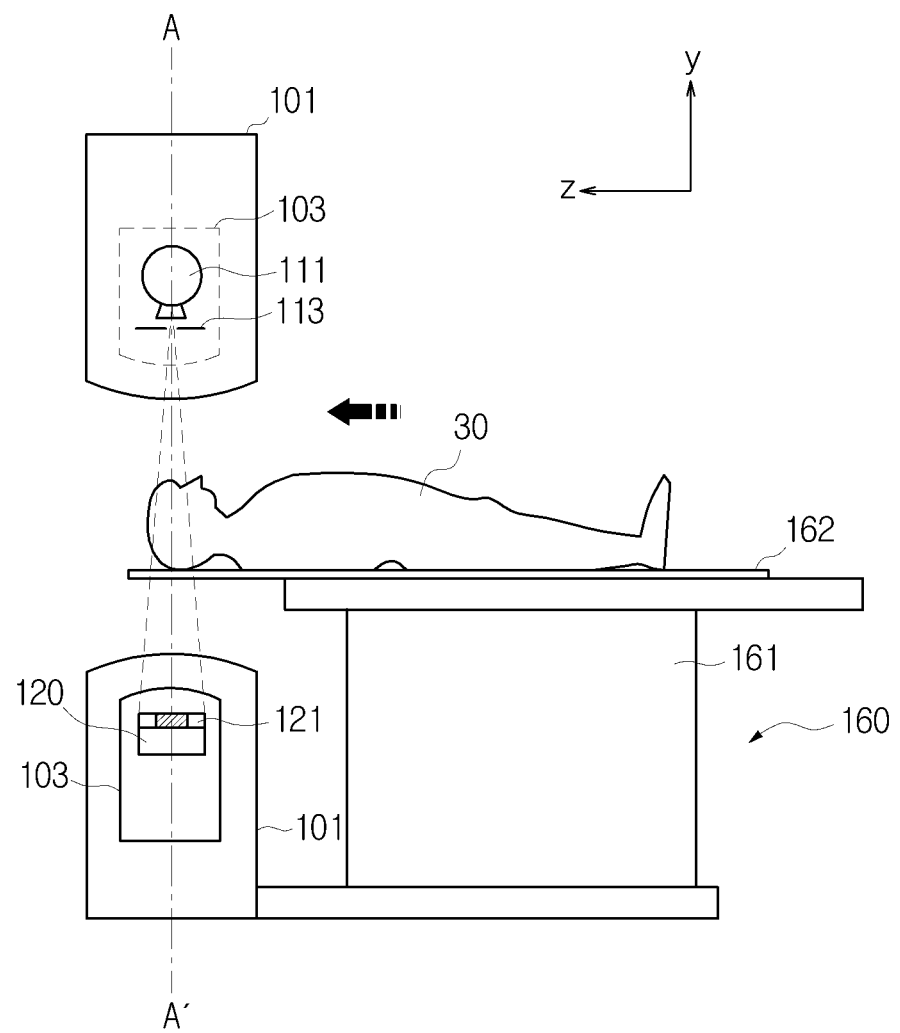
FIGS. 5A and 5B are views illustrating a method of capturing a scout image in a CT apparatus, according to an exemplary embodiment of the present disclosure.
Figure 5B:
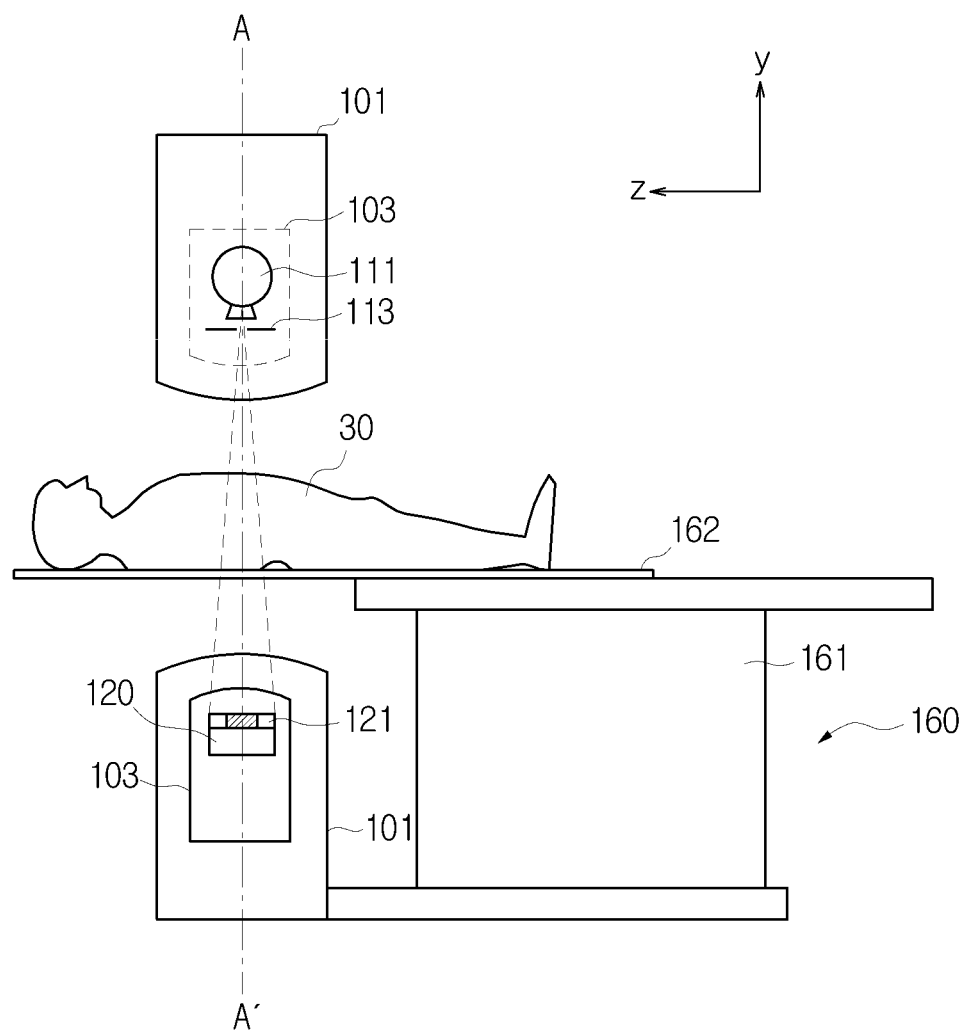

FIGS. 5A and 5B are views illustrating a method of capturing a scout image in the CT apparatus 100, according to an exemplary embodiment of the present disclosure.

Referring to FIG. 5A, the X-ray source 111 and the X-ray detector 120 are arranged to face each other, and are able to rotate around the z-axis by rotation of the gantry 103.

The subject 30 is put on one side of the patient table 162. The patient table 162 is movable along the z-axis, and moves the subject 30 into the inside of the bore 105.

The scout image is an image for establishing a scanning region, and may thus include information regarding a predetermined region of the subject 30, including the scanning region. Accordingly, the predetermined region of the subject 30 may be scanned by moving the patient table 162 in the direction parallel with the rotating shaft of the gantry 103.

For example, X-rays may be irradiated to the head of the subject 30, as shown in FIG. 5A. When the patient table 162 is controlled to be moved in the direction of the arrow shown in FIG. 5A, the subject 30 is moved along with the patient table 162. As a result, X-rays may be irradiated to the abdomen of the subject 30, as shown in FIG. 5B. In this way, the subject 30 may be scanned from head to abdomen.

In this case, the gantry 103 may not be rotated, thus to fix the position of the X-ray source 111 and X-ray detector 120. As shown in FIGS. 5A and 5B, the X-ray source 111 fixed at a position obtains a scout image, which is a cross-sectional image of the subject 30 in the xz-plane by irradiating X-rays to the moving subject 30.

In an exemplary embodiment of the CT apparatus 100, providing substance images separated from the scout image may facilitate the user to establish a scanning region.

A method of creating substance images will now be described in connection with FIGS. 6A to 8C.

Figure 6A:
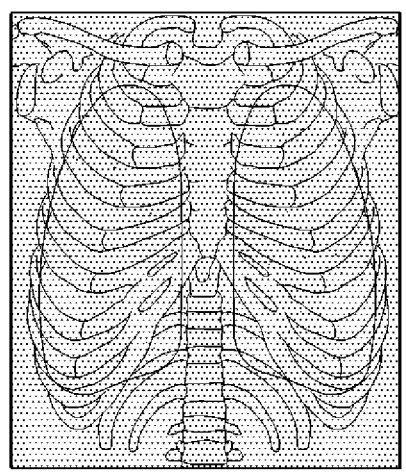
FIGS. 6A, 6B, and 6C are scout images that are obtained by a CT apparatus, according to exemplary embodiments of the present disclosure.
Figure 6B:
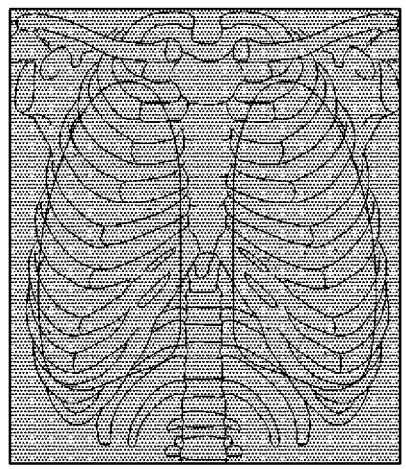
Figure 6C:
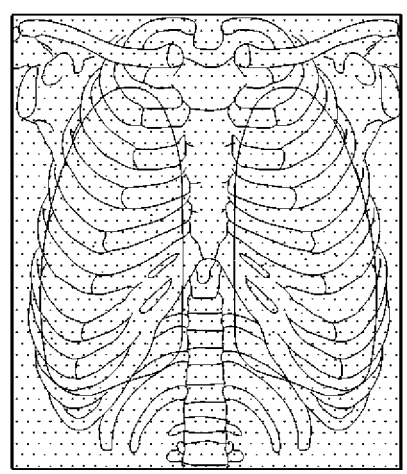
Figure 7A:
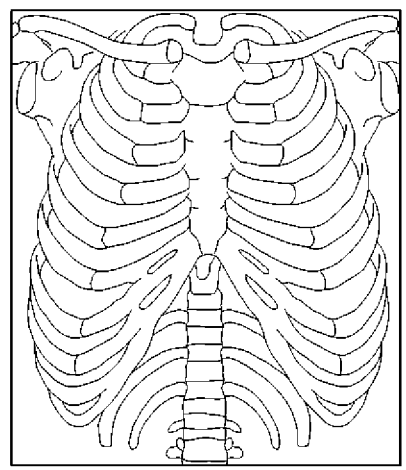
FIGS. 7A and 7B are substance images that are obtained by a CT apparatus, according to exemplary embodiments of the present disclosure.
Figure 7B:
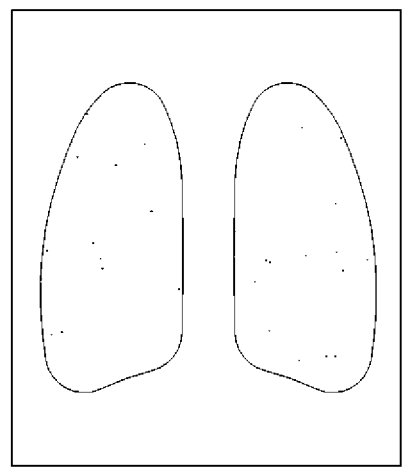
Figure 8A:
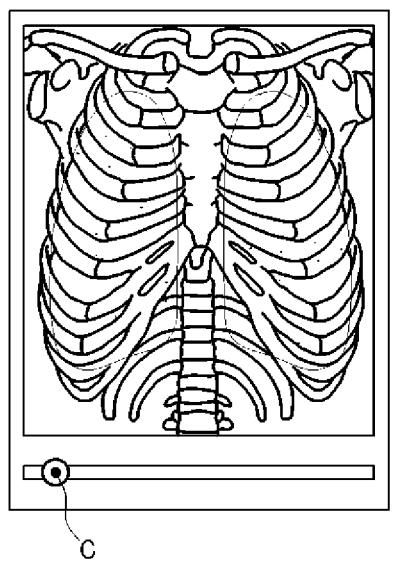
FIGS. 8A, 8B, and 8C are overlaid images that are obtained by overlaying multiple substance images in a CT apparatus, according to exemplary embodiments of the present disclosure.
Figure 8B:
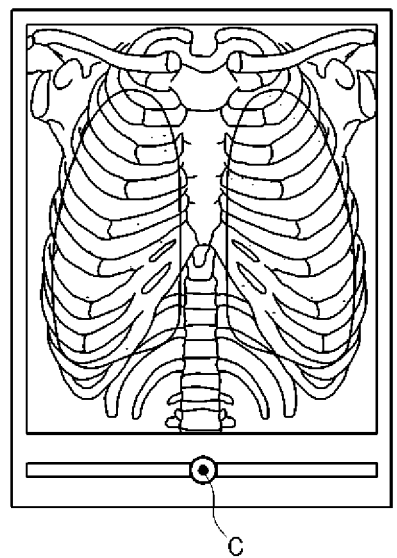
Figure 8C:
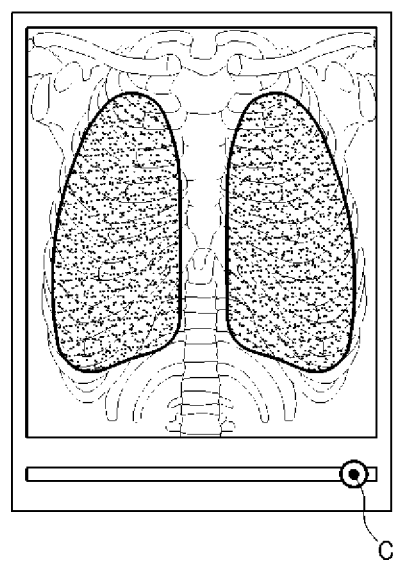

FIGS. 6A, 6B, and 6C are scout images that are obtained by the CT apparatus 100, according to exemplary embodiments of the present disclosure. FIGS. 7A and 7B are substance images that are obtained by the CT apparatus 100, according to exemplary embodiments of the present disclosure. FIGS. 8A, 8B, and 8C are overlaid images that are obtained by overlaying multiple substance images in the CT apparatus 100, according to exemplary embodiments of the present disclosure.

To create a substance image, the X-ray source 111 may irradiate multi-energy X-rays to the subject 30. The X-ray source 111 may irradiate X-rays having a predetermined energy band to the subject 30. The energy band of X-rays to be irradiated may be controlled by the tube voltage.

The X-ray detector 120 may detect X-rays that penetrate the subject 30 and classify them by multiple energy bands.

For this, the X-ray detector 120 may be implemented by a photon counting detector. The photon counting detector may set multiple threshold energy levels, and count photons greater than the respective threshold energy levels to divide them by respective energy bands.

For example, the X-ray detector 120 may divide the detected X-rays by low, middle, and high energy bands.

The X-rays divided by multiple energy bands may be sent to the image processor 130. The image processor 130 may use the X-rays divided by the multiple energy bands to obtain multiple scout images for the multiple energy bands.

Given the X-rays divided by low, middle, and high energy bands, the image processor 130 may obtain a scout image for the low energy band (hereinafter, referred to as a low energy scout image), a scout image for the middle energy band (a middle energy scout image), and a scout image for the high energy band (a high energy scout image).

For example, FIGS. 6A, 6B, and 6C are a low energy scout image, a middle energy scout image, and a high energy scout image, respectively. The display 142 displays the low energy scout image, the middle energy scout image, and the high energy scout image.

The image processor 130 may separate multiple substance images from the multiple scout images obtained as described above.

An attenuation coefficient refers to what numerically represents an extent of X-ray deterioration, and may vary by substances inside the subject 30, or energy bands of X-rays irradiated.

Based on this property, the image processor 130 may obtain multiple substance images using the multiple scout images.

For example, FIGS. 7A and 7B are an image of bones and an image of tissues, among the substance images separated from the multiple scout images, respectively.

The display 142 displays the substance images separated in this way. Compared with the scout image, the substance images may have clear boundaries of substances that make up the subject 30.

The input interface 141 may receive a scanning region on the displayed substance image. The scanning region may be a target for CT scanning.

The display 142 may display the substance image in various ways. Exemplary embodiments of a method of overlaying and displaying substance images will be described in connection with FIGS. 8A to 8C.

The display 142 may display at least two of substance images separated from multiple scout images by overlaying them. Transparency of an overlaid substance image may be determined according to an input of the user.

For example, referring to each of FIGS. 8A to 8C, the display 142 displays an image of bones and an image of tissues by overlaying them. If the user wants to emphasize the image of tissues, the user may increase opaqueness of the image of tissues. As a result, the user may check the tissue arrangement as well as the outline of the bones.

Referring to FIGS. 8A to 8C, the display 142 displays overlaid images in which substance images have different opaqueness controlled by the location of a control bar c. As shown in FIG. 8A, where the control bar c is on the left, the display 142 displays overlaid images in which an image of bones has higher opaqueness than an image of tissues. As shown in FIG. 8B, where the control bar c is on the center, the display 142 displays overlaid images in which the image of bones has the same opaqueness as that of the image of tissues. As shown in FIG. 8C, where the control bar c is on the right, the display 142 displays overlaid images in which an image of tissues has higher opaqueness than an image of bones.

The user may be provided with overlaid images in which a desired substance is emphasized by manipulating the control bar.

Alternatively, the display 142 may display at least one of the multiple scout images and at least one of the multiple substance images by overlaying them.

Figure 9:
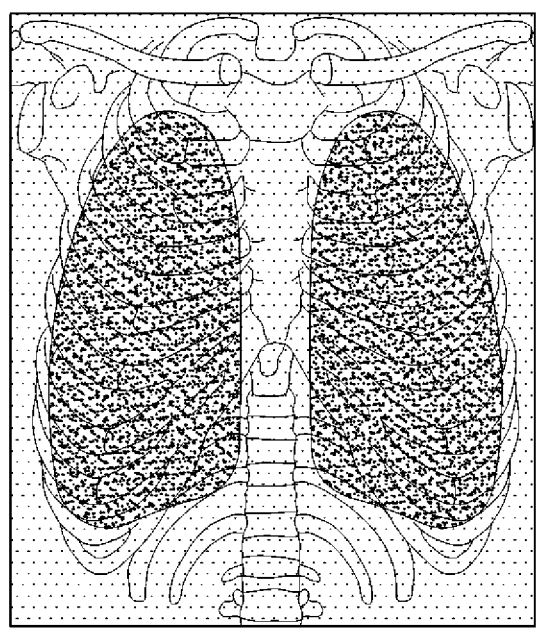
FIG. 9 is a view illustrating a method of displaying a substance image in a CT apparatus, according to an exemplary embodiment of the present disclosure.

FIG. 9 is a view illustrating a method of displaying a substance image in the CT apparatus 100, according to an exemplary embodiment of the present disclosure.

Referring to FIG. 9, the display 142 displays a high energy image of a plurality of scout images and an image of tissues of a plurality of substance images by overlaying them.

To emphasize the image of tissues, it may also be possible to display the image of tissues by further increasing the opaqueness of the image of tissues. As such, emphasizing a substance of interest in a scout image may help the user easily establish a scanning region.

Furthermore, the display 142 may match at least one of the plurality of substance images with a reference organ image, and display the matching result. A scanning region may be determined by a region where an organ inside the subject 30 exists, and thus providing the position of the reference organ image may help the user easily establish the scanning region.

An organ as herein used may refer to an organ inside the subject 30, such as the heart, liver, lung, etc., identified by its function, and each organ may be made of one or more substances that make up the subject 30. A reference organ image may be an image obtained by modeling the subject 30, e.g., an organ of a human body. The reference organ image may be determined by obtaining information about the organ of the subject 30 from a predetermined sample. For example, information about an organ, such as the feature information of the organ may be obtained from a predetermined sample, and a reference organ image may be created based on an average of a plurality of pieces of information obtained from the sample. Respective reference organ images may be created for a plurality of organs of the subject 30.

A method of obtaining the reference organ image may employ Atlas modeling, but is not limited thereto.

The controller 150 may match a reference organ image to a substance image.

Figure 10A:
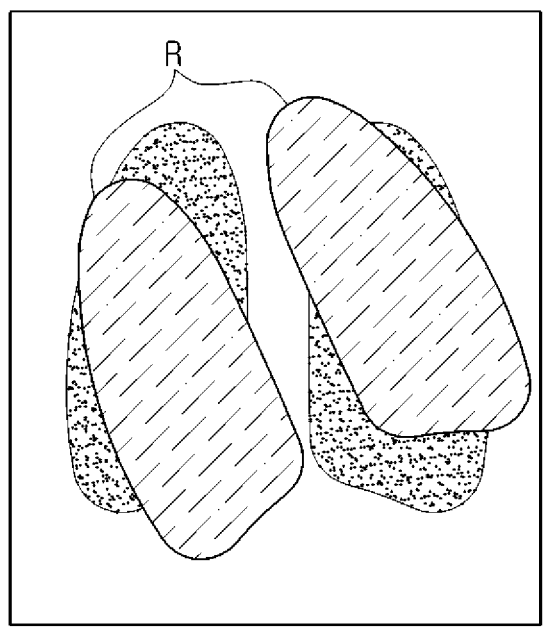
FIGS. 10A, 10B, and 10C are views illustrating a method of matching a reference organ image to a substance image in a CT apparatus, according to an exemplary embodiment of the present disclosure.
Figure 10B:
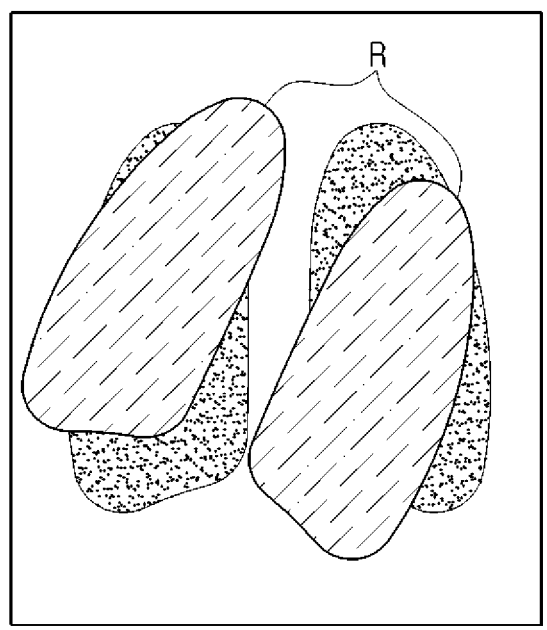
Figure 10C:
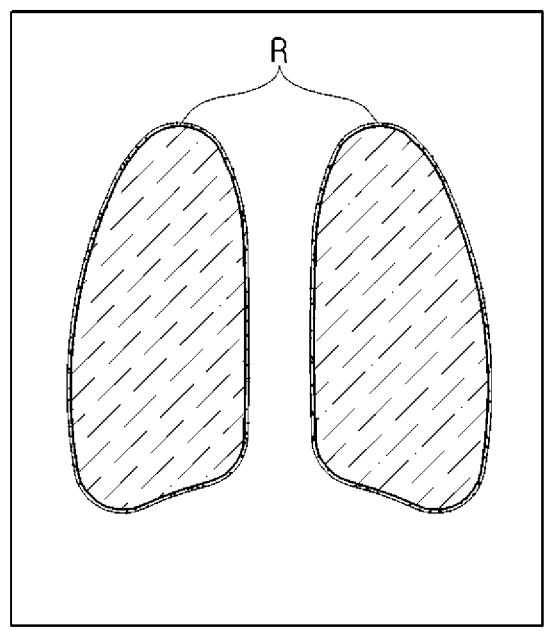

FIGS. 10A, 10B, and 10C are views illustrating a method of matching a reference organ image to a substance image in the CT apparatus 100, according to an exemplary embodiment of the present disclosure.

In FIGS. 10A to 10C, a method of matching a reference organ image to an image of tissues shown in FIG. 7B among a plurality of substance images is illustrated. Image R may refer to a reference organ image.

As the reference organ image may be created based on the organ obtained from a predetermined sample, it may represent a feature of the organ. Accordingly, a region, which is most similar to the reference organ image, may be checked in a substance image separated from a scout image, to match the coordinates of the two images.

As shown in FIGS. 10A and 10B, the region most similar to the reference organ image may be found by varying the reference organ image R in the fixed image of the substance. Consequently, as shown in FIG. 10C, the reference organ image R is matched to the substance image.

The display 142 displays a result of matching the reference organ image to the substance image. At this time, the display 142 may emphasize the reference organ image R.

As such, matching a reference organ image to a substance image may enable the boundary and feature of the substance to be seen more clearly.

Furthermore, the display 142 may also display the resultant image from matching the reference organ image to the substance image to overlay at least one of the plurality of scout images.

Figure 11:
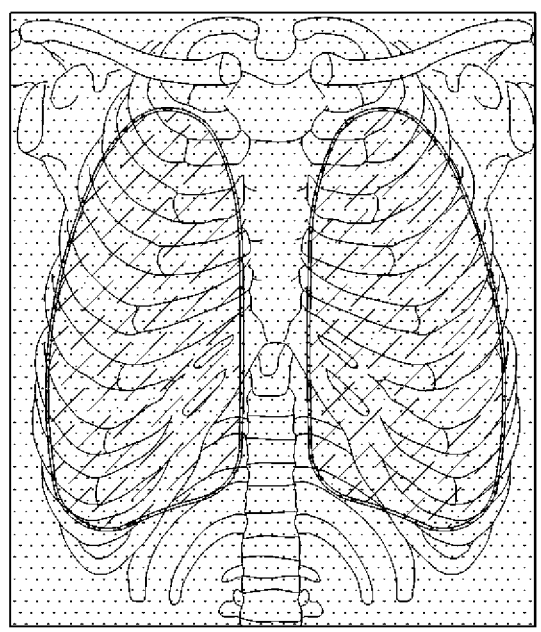
FIG. 11 is a view illustrating a method of displaying a substance image in a CT apparatus, according to another exemplary embodiment of the present disclosure.

FIG. 11 is a view illustrating a method of displaying a substance image in the CT apparatus 100, according to another exemplary embodiment of the present disclosure.

The display 142 may display a matched image obtained by matching a reference organ image to a substance image, and a scout image by overlaying them.

For example, as shown in FIG. 11, the display 142 displays the matched image and a high energy scout image of FIG. 6C by overlaying them.

To emphasize the matched image, opaqueness of the matched image may be increased. As such, emphasizing a substance region in a scout image may help the user easily establish a scanning region.

Referring again to FIG. 2, the display 142 may also display a recommended scanning region based on the matched image obtained by matching the reference organ image to the substance image. As the reference organ image represents a feature of an organ, the display 142 may display a region of the substance image corresponding to the reference organ image as a recommended scanning region.

For this, the input interface 141 may receive an organ of interest among many different internal organs of the subject 30. For example, when the user inputs organ A through the input interface 141 as an organ of interest, the display 142 may match a reference organ image for the organ A to a substance image and display the resultant image.

The display 142 may indicate a recommended scanning region on the displayed substance image. Displaying both the substance image and the recommended scanning region may offer the user a precise position of the recommended scanning region.

In accordance with the aforementioned exemplary embodiments, the display 142 may display at least one of a plurality of substance images. The user may visually check this, and then designate a scanning region through the input interface 141.

Once the scanning region is designated, the controller 150 may perform CT scanning for the scanning region by rotating the gantry 103.

Alternatively, in another exemplary embodiment of the CT apparatus 100, the controller 150 may determine the scanning region based on at least one of the plurality of substance images.

For this, the controller 150 may determine the scanning region by comparing at least one of the plurality of substance images and a predetermined reference organ image. The controller 150 may compare the substance image and the reference organ image after matching the reference organ image to the at least one of the plurality of substance images.

For the controller 150 to determine the scanning region, the user may input an organ of interest through the input interface 141. For example, when the user inputs organ A as an organ of interest, the controller 150 may compare the substance image and a reference organ image for the organ A.

As a result, the controller 150 may determine a scanning region for the input organ of interest. The controller 150 may determine a scanning region to include a region where the organ A is displayed, by comparing the substance image and the reference organ image.

Figure 12:
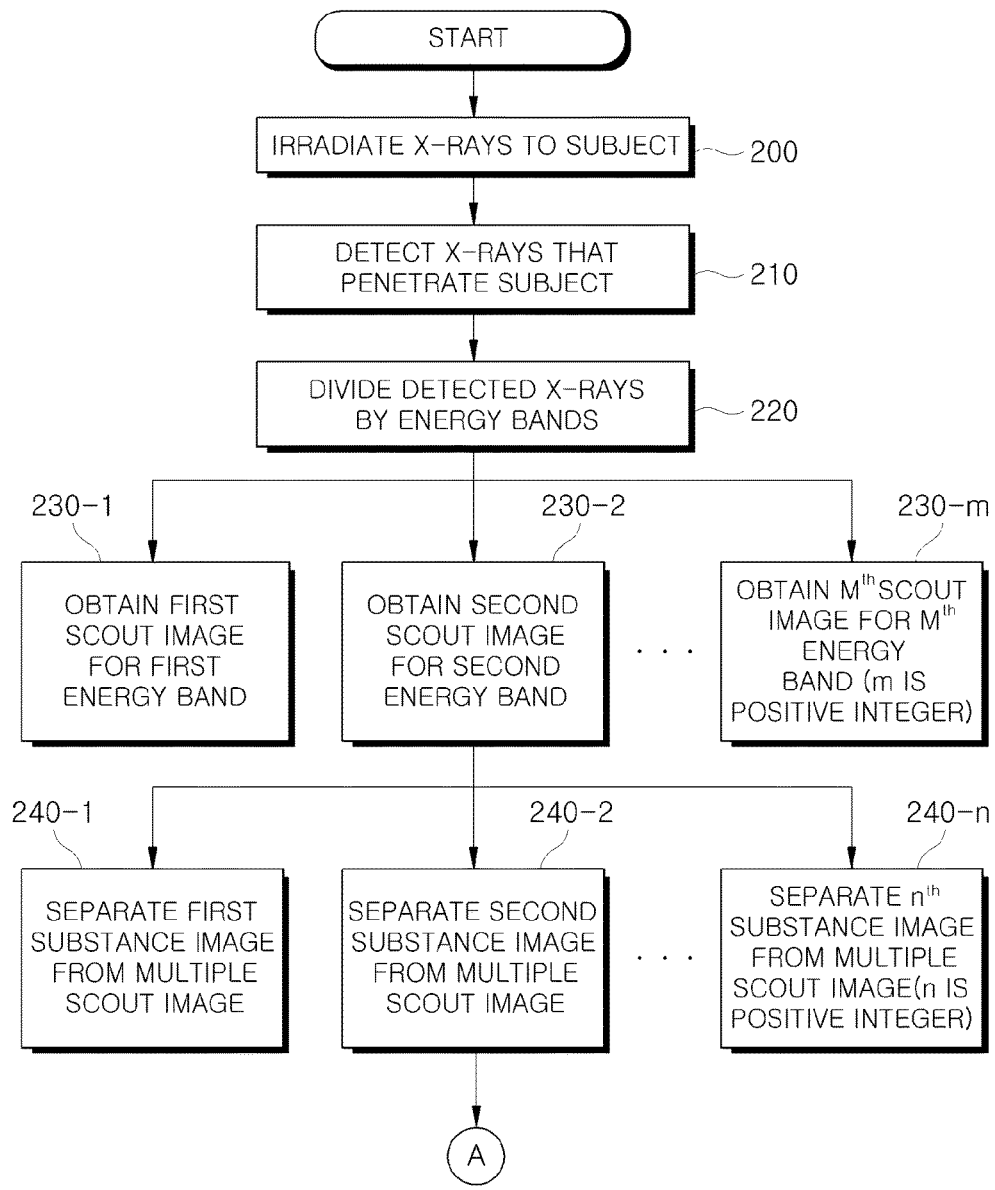
FIG. 12 is a flowchart illustrating a method of creating multiple substance images included in a method of controlling a CT apparatus, according to an exemplary embodiment of the present disclosure.

FIG. 12 is a flowchart illustrating a method of creating multiple substance images included in a method of controlling a CT apparatus, according to an exemplary embodiment of the present disclosure.

First, X-rays are irradiated to a subject, in operation 200. X-rays may be irradiated to the subject while the subject is moving in the direction parallel with a rotating shaft of the gantry 103.

The X-rays irradiated may be multi-energy X-rays.

Next, X-rays that penetrate the subject are detected, in operation 210. The X-rays penetrating the subject may be detected by a photon counting detector.

The detected X-rays are divided by energy bands, in operation 220. As the multi-energy X-rays are irradiated to the subject, the detected X-rays may also have a wide spectrum of energy. The wide spectrum of energy may be divided into multiple energy bands, and the detected X-rays may be divided by the multiple energy bands.

With the divided X-rays, a scout image may be obtained. The scout image may be an image for establishing a scanning region before CT scanning.

A first scout image for a first energy band of the multiple energy bands is obtained, in operation 230-1. The first scout image for the first energy band may be obtained based on the detected X-rays that have the first energy band.

At the same time, a second scout image for a second energy band is obtained, in operation 230-2. Likewise, an $m^{th}$ scout image for an $m^{th}$ energy band is obtained, in operation 230-$m$. Consequently, m scout images may be obtained. m is a positive integer.

An image of a first substance of a plurality of substances that make up the subject is separated from the m scout images, in operation 240-1. To separate the substance image, an attenuation coefficient may be used.

At the same time, an image of a second substance of the plurality of substances is separated from the m scout images, in operation 240-2. Likewise, an image of an $n^{th}$ substance of the plurality of substances is separated from the m scout images, in operation 240-$n$. Consequently, n substance images may be obtained. n is a positive number.

Figure 13:
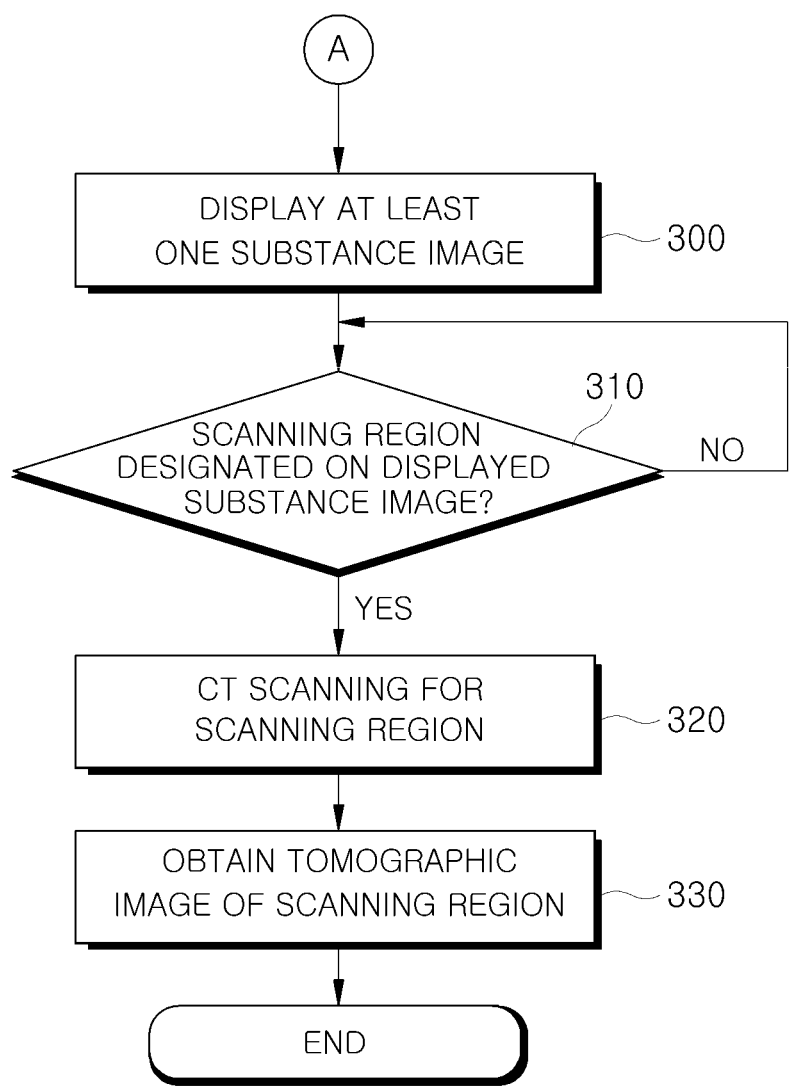
FIG. 13 is a flowchart illustrating a method of displaying multiple substance images included in a method of controlling a CT apparatus, according to an exemplary embodiment of the present disclosure.

FIG. 13 is a flowchart illustrating a method of displaying multiple substance images included in a method of controlling the CT apparatus, according to an exemplary embodiment of the present disclosure.

First, at least one substance image of a plurality of substance images is displayed, in operation 300. The substance image to be displayed may be determined by an organ of interest input by the user.

Next, it is determined whether a scanning region is designated on the displayed substance image, in operation 310 by an input from the user. If no scanning region is designated, checking the input from the user may be repeatedly performed.

Otherwise, if the scanning region is designated, CT scanning for the scanning region is performed, in operation 320. As a result, a tomographic image of the scanning region is obtained, in operation 330.

Figure 14:
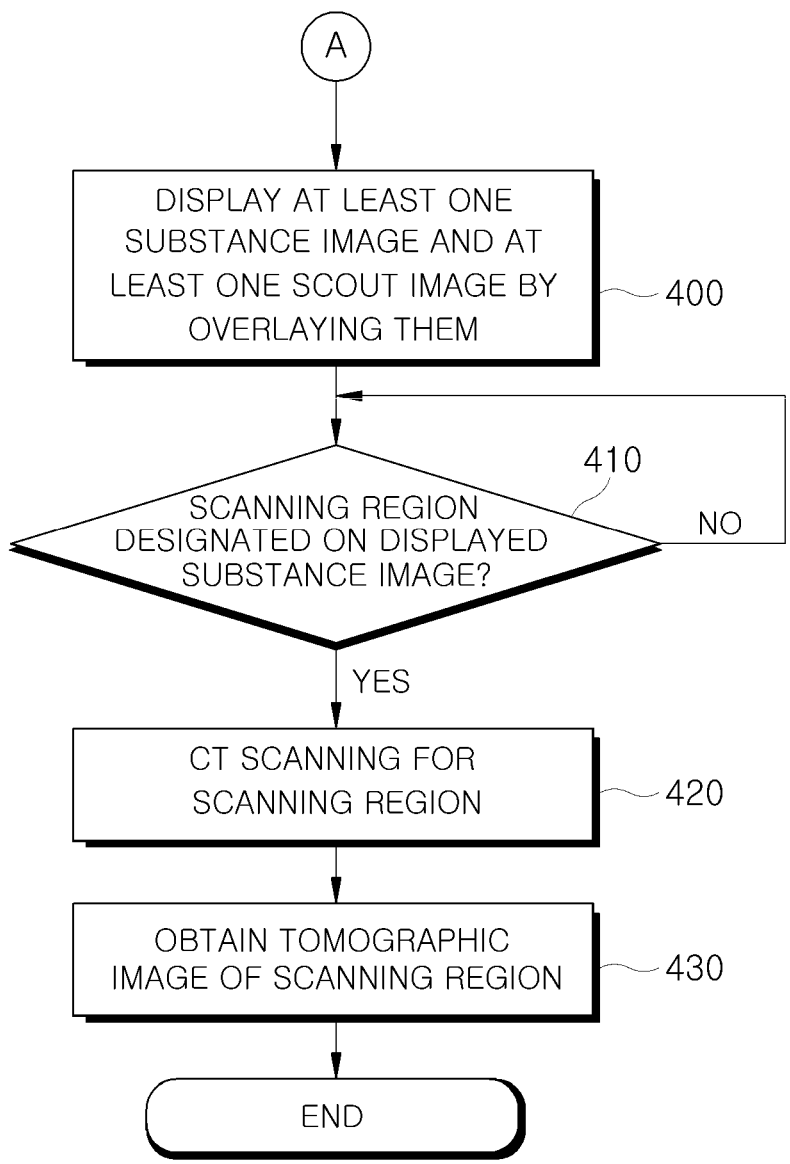
FIG. 14 is a flowchart illustrating a method of displaying multiple substance images included in a method of controlling a CT apparatus, according to another exemplary embodiment of the present disclosure.

FIG. 14 is a flowchart illustrating a method of displaying multiple substance images included in a method of controlling a CT apparatus, according to another exemplary embodiment of the present disclosure.

First, at least one substance image of multiple substance images and at least one scout image of multiple scout images are displayed by overlaying them, in operation 400. The substance image to be displayed may be determined by an organ of interest input by the user.

The substance image and the scout image may be displayed by varying their respective opaqueness. For example, to emphasize the substance image for display, the opaqueness of the substance image may be increased.

Next, it is determined whether a scanning region is designated on the displayed substance image by an input from the user, in operation 410. If no scanning region is designated, checking the input from the user may be repeatedly performed.

Otherwise, if the scanning region is designated, CT scanning for the scanning region is performed, in operation 420. As a result, a tomographic image of the scanning region is obtained, in operation 430.

Displaying the substance image and the scout image to overlay each other may offer the user more precise information for establishing a scanning region.

Figure 15:
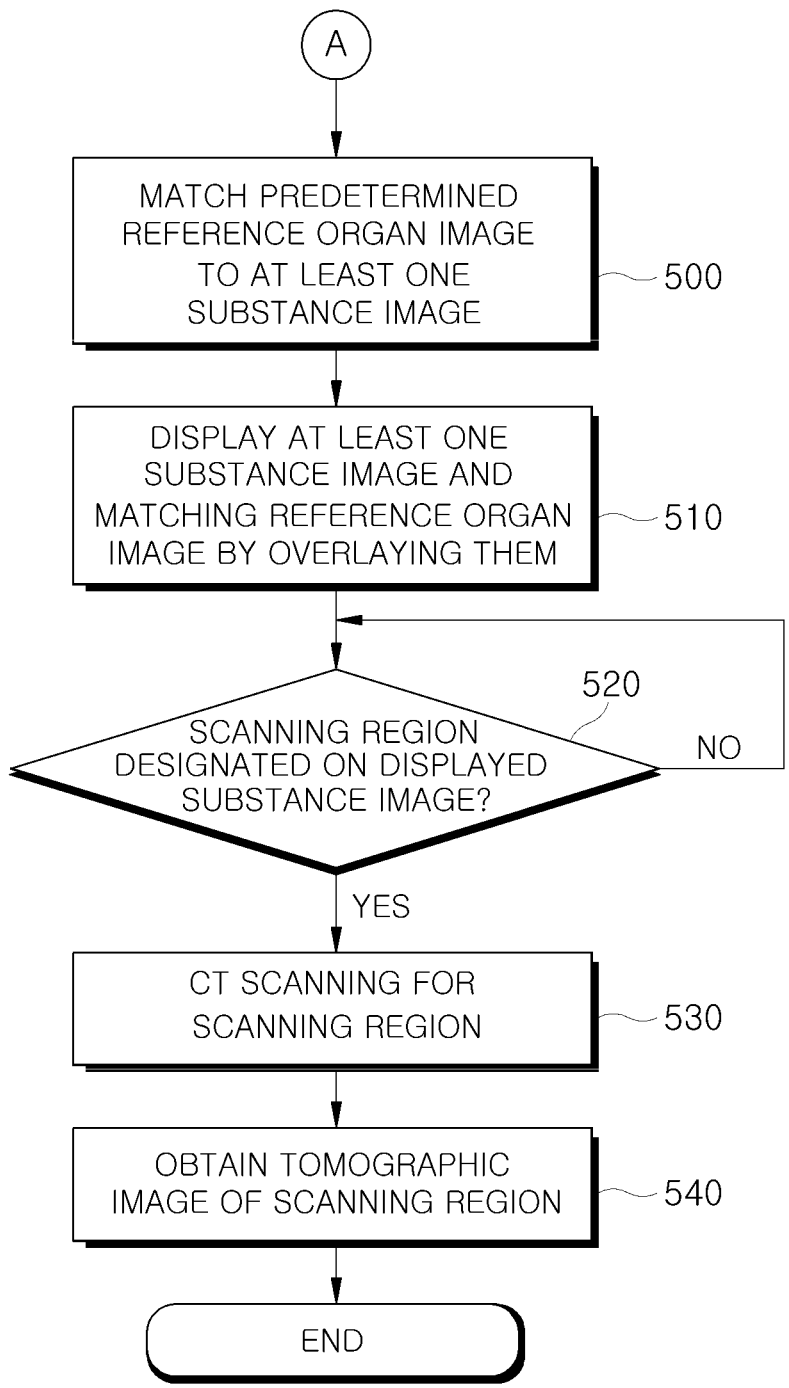
FIG. 15 is a flowchart illustrating a method of displaying multiple substance images included in a method of controlling a CT apparatus, according to another exemplary embodiment of the present disclosure.

FIG. 15 is a flowchart illustrating a method of displaying multiple substance images included in a method of controlling a CT apparatus, according to another exemplary embodiment of the present disclosure.

First, a predetermined reference organ image is matched to at least one substance image of multiple substance images, in operation 500. The substance image and the reference organ image to be displayed may be determined by an organ of interest input by the user.

A reference organ image may be an image obtained by modeling a subject, e.g., an organ of a human body. A method of obtaining the reference organ image may employ Atlas modeling, but is not limited thereto.

Next, the at least one substance image and the matching reference organ image are displayed by overlaying them, in operation 510. The substance image and the reference organ image may be displayed by varying their respective opaqueness. For example, to emphasize the reference organ image for display, the opaqueness of the reference organ image may be increased.

Next, it is determined whether a scanning region is designated on the displayed substance image by an input from the user, in operation 520. If no scanning region is designated, checking the input from the user may be repeatedly performed.

Otherwise, if the scanning region is designated, CT scanning for the scanning region is performed, in operation 530. As a result, a tomographic image of the scanning region is obtained, in operation 540.

Matching the substance image and the reference organ image may offer the user more precise position of the organ.

Figure 16:
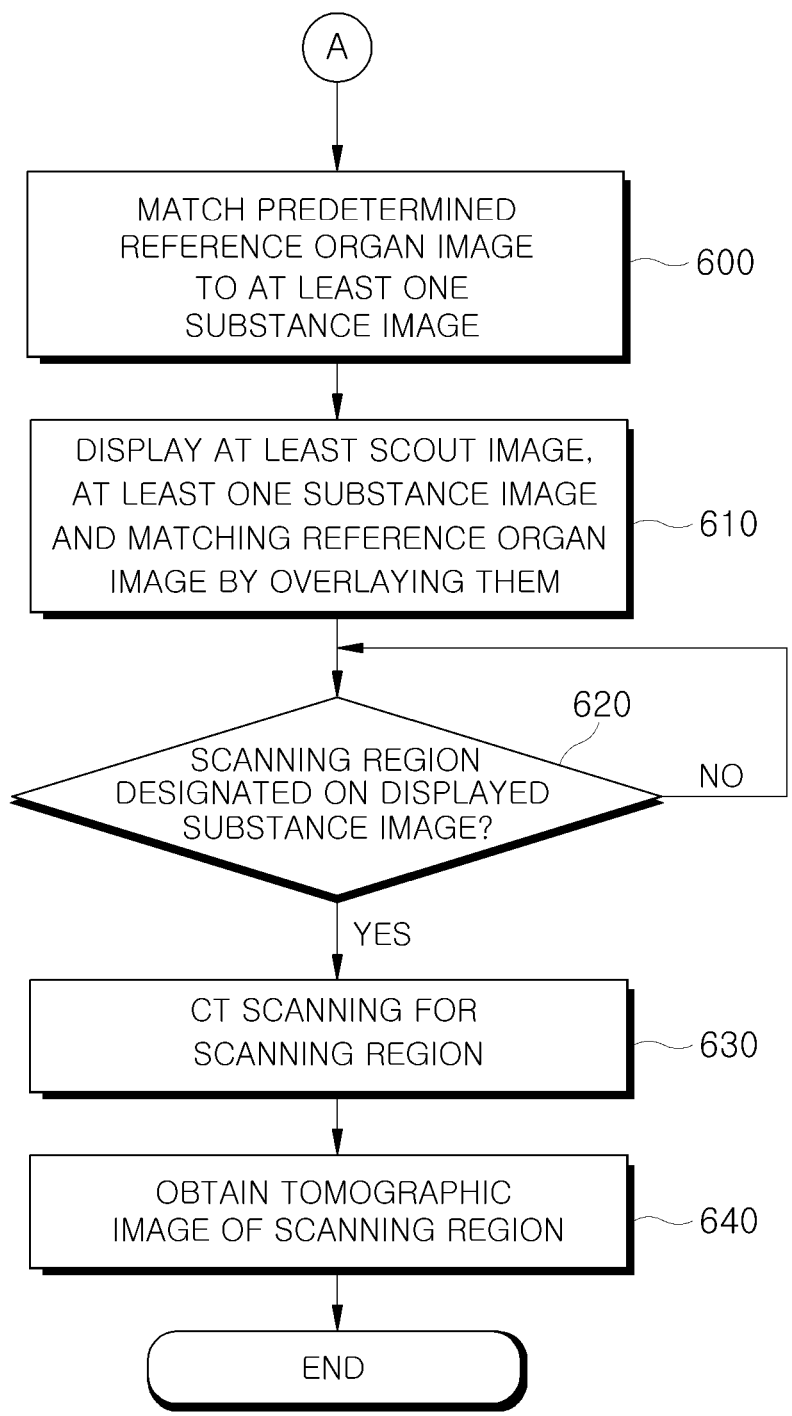
FIG. 16 is a flowchart illustrating a method of displaying multiple substance images included in a method of controlling a CT apparatus, according to another exemplary embodiment of the present disclosure.

FIG. 16 is a flowchart illustrating a method of displaying multiple substance images included in a method of controlling a CT apparatus, according to another exemplary embodiment of the present disclosure.

First, a predetermined reference organ image is matched to at least one substance image of multiple substance images, in operation 600. The substance image and the reference organ image to be displayed may be determined by an organ of interest input by the user.

Next, at least one scout image of multiple scout images, the at least one substance image, and the matching reference organ image are displayed by overlaying them, in operation 610. The substance image and the reference organ image may be displayed by varying their respective opaqueness. For example, to emphasize the reference organ image for display, the opaqueness of the reference organ image may be increased.

Next, it is determined whether a scanning region is designated on the displayed substance image by an input from the user, in operation 620. If no scanning region is designated, checking the input from the user may be repeatedly performed.

Otherwise, if the scanning region is designated, CT scanning for the scanning region is performed, in operation 630. As a result, a tomographic image of the scanning region is obtained, in operation 640.

FIG. 17 is a flowchart illustrating a method of displaying multiple substance images included in a method of controlling the CT apparatus, according to another exemplary embodiment of the present disclosure.

First, a predetermined reference organ image is matched to at least one substance image of multiple substance images, in operation 700. The substance image and the reference organ image to be displayed may be determined by an organ of interest input by the user.

A reference organ image may be an image obtained by modeling a subject, e.g., an organ of a human body. A method of obtaining the reference organ image may employ Atlas modeling, but is not limited thereto.

Next, the at least one substance image and the matching reference organ image are displayed by overlaying them, and at the same time, a scanning region is recommended on the displayed image, in operation 710. Both the overlay image and the recommended scanning region may be displayed together.

Next, it is determined whether a scanning region is designated on the displayed substance image by an input from the user, in operation 720. If no scanning region is designated, checking the input from the user may be repeatedly performed.

Otherwise, if the scanning region is designated, CT scanning for the scanning region is performed, in operation 730. As a result, a tomographic image of the scanning region is obtained, in operation 740.

Recommending the scanning region to be a region similar to the reference organ image may help the user establish a more precise scanning region.

FIG. 18 is a flowchart illustrating a method of controlling a CT apparatus, according to an exemplary embodiment of the present disclosure.

First, a predetermined reference organ image is matched to at least one substance image of multiple substance images, in operation 800. The substance image and the reference organ image to be displayed may be determined by an organ of interest input by the user.

A reference organ image may be an image obtained by modeling a subject, e.g., an organ of a human body. A method of obtaining the reference organ image may employ Atlas modeling, but is not limited thereto.

Next, a scanning region is determined by comparing the at least one substance image and the matching reference organ image, in operation 810. A region most similar to the reference organ image may be determined to be the scanning region in the substance image.

Once the scanning region is determined, CT scanning for the scanning region is performed, in operation 820. As a result, a tomographic image of the scanning region is obtained, in operation 830.

Such active determination of the scanning region without separate input from the user may increase convenience for the user.

According to the exemplary embodiments of a CT apparatus and method of controlling the same, an image of a constituent substance (or a substance image) of a subject may be provided for the user, facilitating establishment of a more precise scanning region.

Furthermore, a scanning region may be actively established based on an internal organ input by the user. This eliminates intervention of the user to input a separate scanning region, and thus includes less additional operations other than CT scanning.

In addition, the exemplary embodiments may also be implemented through computer-readable code and/or instructions on a medium, e.g., a non-transitory computer-readable medium, to control at least one processing element to implement any above-described exemplary embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments and advantages are exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A computed tomographic (CT) apparatus comprising:
an X-ray scanner including:
an X-ray source configured to radiate X-rays to a subject; and
an X-ray detector configured to detect the X-rays penetrating the subject, and
divide the detected X-rays by energy bands;
an image processor configured to generate scout images based on the X-rays divided by the energy bands, and generate substance images of substances of the subject based on the scout images;
a display configured to display at least one of the substance images; and
an input interface configured to receive a scanning region for the displayed at least one of the substance images.

2. The CT apparatus of claim 1, wherein the X-ray scanner further includes a gantry on which the X-ray source and the X-ray detector are arranged to face each other.

3. The CT apparatus of claim 2, wherein the gantry comprises a rotating shaft, and
the X-ray scanner is further configured to:
radiate the X-rays to the subject moving in a direction parallel to the rotating shaft of the gantry; and
perform CT scanning by rotating the gantry and radiating X-rays to the received scanning region.

4. The CT apparatus of claim 1, wherein the image processor is further configured to separate the substance images from the scout images.

5. The CT apparatus of claim 1, wherein the display is further configured to display the at least one of the substance images and a scout image of the scout images, the displayed at least one of the substance images and the displayed scout image overlaying each other.

6. The CT apparatus of claim 1, wherein the image processor is further configured to match the at least one of the substance images to a reference organ image that is determined based on information of an organ of the subject that is obtained from a sample, and
the display is further configured to display a result of the at least one of the substance images matched to the reference organ image.

7. The CT apparatus of claim 6, wherein the display is further configured to display the result of the at least one of the substance images matched to the reference organ image, along with a scout image of the scout images, the displayed result of the at least one of the substance images matched to the reference organ image and the displayed scout image overlaying each other.

8. The CT apparatus of claim 6, wherein the display is further configured to emphasize an organ region in the reference organ image.

9. The CT apparatus of claim 1, wherein the input interface is further configured to receive an organ of interest among internal organs of the subject.

10. The CT apparatus of claim 9, wherein the display is further configured to display the organ of interest as a recommended scanning region.

11. A computed tomographic (CT) apparatus comprising:
an X-ray scanner including:
an X-ray source configured to radiate X-rays to a subject; and
an X-ray detector configured to detect the X-rays penetrating the subject, and divide the detected X-rays by energy bands;
an image processor configured to generate scout images based on the X-rays divided by the energy bands, and generate substance images of substances of the subject based on the scout images; and
a controller configured to determine a scanning region of the subject based on at least one of the substance images.

12. The CT apparatus of claim 11, wherein the X-ray scanner further includes a gantry on which the X-ray source and the X-ray detector are arranged to face each other.

13. The CT apparatus of claim 12, wherein the gantry comprises a rotating shaft, and
the X-ray scanner is further configured to:
radiate the X-rays to the subject moving in a direction parallel to the rotating shaft of the gantry; and
perform CT scanning by rotating the gantry and radiating X-rays to the determined scanning region.

14. The CT apparatus of claim 11, wherein the image processor is further configured to separate the substance images from the scout images.

15. The CT apparatus of claim 11, wherein the controller is further configured to determine the scanning region by comparing the at least one of the substance images and a reference organ image.

16. The CT apparatus of claim 11, wherein the controller is further configured to:
match the at least one of the substance images to a reference organ image; and
determine the scanning region by comparing the matched at least one of the substance images and the matched reference organ image.

17. The CT apparatus of claim 11, further comprising an input interface configured to receive an organ of interest among internal organs of the subject.

18. The CT apparatus of claim 17, wherein the controller is further configured to determine the scanning region based on the organ of interest.

19. A method of controlling a computed tomographic (CT) apparatus, the method comprising:
radiating X-rays to a subject;
detecting the X-rays penetrating the subject;

dividing the detected X-rays by energy bands;
generating scout images based on the X-rays divided by the energy bands;
generating substance images of substances of the subject based on the scout images;
displaying at least one of the substance images; and
receiving a scanning region for the displayed at least one of the substance images.

20. The method of claim 19, wherein the radiating X-rays to the subject comprises radiating X-rays to the subject moving in a direction parallel to a rotating shaft of a gantry.

21. The method of claim 19, further comprising performing CT scanning by rotating a gantry and radiating X-rays to the received scanning region.

22. The method of claim 19, wherein the displaying the at least one of the substance images comprises displaying the at least one of the substance images and a scout image of the scout images, the displayed at least one of the substance images and the displayed scout image overlaying each other.

23. The method of claim 19, further comprising matching the at least one of the substance images to a reference organ image, and
wherein the displaying the at least one of the substance images comprises displaying a result of the matching.

24. The method of claim 19, further comprising:
receiving an organ of interest among internal organs of the subject; and
displaying the organ of interest as a recommended scanning region.

25. A method of controlling a computed tomographic (CT) apparatus, the method comprising:
radiating X-rays to a subject;
detecting the X-rays penetrating the subject;
dividing the detected X-rays by energy bands;
generating scout images based on the X-rays divided by the energy bands;
generating substance images of substances of the subject based on the scout images; and
determining a scanning region of the subject based on at least one of the substance images.

26. The method of claim 25, wherein the radiating X-rays to the subject comprises radiating X-rays to the subject moving in a direction parallel to a rotating shaft of a gantry.

27. The method of claim 25, further comprising performing CT scanning by rotating a gantry and radiating X-rays to the determined scanning region.

28. The method of claim 25, further comprising matching the at least one of the substance images to a reference organ image,
wherein the determining the scanning region of the subject comprises determining the scanning region by comparing the matched at least one of the substance images and the matched reference organ image.

29. The method of claim 25, further comprising receiving an organ of interest among internal organs of the subject,
wherein the determining the scanning region of the subject comprises determining the scanning region based on the organ of interest.

* * * * *